US012685747B2

(12) United States Patent
Jermy et al.

(10) Patent No.: US 12,685,747 B2
(45) Date of Patent: Jul. 21, 2026

(54) DRUG DELIVERY SYSTEM

(71) Applicant: Imam Abdulrahman Bin Faisal University, Dammam (SA)

(72) Inventors: B. Rabindran Jermy, Dammam (SA); Vijaya Ravinayagam, Dammam (SA); Dana Almohazey, Dammam (SA); Hend Ghnaim, Dammam (SA); Eman Al-Abbad, Dammam (SA)

(73) Assignee: Imam Abdulrahman Bin Faisal University, Dammam (SA)

( * ) Notice: Subject to any disclaimer, the term of this patent is extended or adjusted under 35 U.S.C. 154(b) by 242 days.

(21) Appl. No.: 18/773,253

(22) Filed: Jul. 15, 2024

(65) Prior Publication Data

US 2026/0014197 A1 Jan. 15, 2026

(51) Int. Cl.

| | |
|---|---|
| ***A61K 33/243*** | (2019.01) |
| ***A61K 9/50*** | (2006.01) |
| ***A61K 9/51*** | (2006.01) |
| ***A61M 5/00*** | (2006.01) |

(52) U.S. Cl.

CPC .......... *A61K 33/243* (2019.01); *A61K 9/5031* (2013.01); *A61K 9/5115* (2013.01); *A61K 9/5123* (2013.01); *A61M 5/00* (2013.01)

(58) Field of Classification Search

CPC .. A61K 33/243; A61K 9/5031; A61K 9/5115; A61K 9/5123; A61K 9/143; A61K 9/5146; A61M 5/00

See application file for complete search history.

(56) References Cited

U.S. PATENT DOCUMENTS

| | | | |
|---|---|---|---|
| 2011/0305765 A1 | 12/2011 | Mathur et al. |
| 2021/0115071 A1 | 4/2021 | Sun et al. |
| 2022/0387335 A1 | 12/2022 | MohanKumar et al. |

FOREIGN PATENT DOCUMENTS

| | | |
|---|---|---|
| CN | 110652497 B | 7/2020 |
| WO | WO 2005/095031 A1 | 10/2005 |

OTHER PUBLICATIONS

Baeza, A. et al., “Recent advances in porous nanoparticles for drug delivery in antitumoral applications: inorganic nanoparticles and nanoscale metal-organic frameworks”, Expert Opinion on Drug Delivery, 2016, 47 total pages.

Thirumurugan, A., et al., “Green synthesis of platinum nanoparticles using Azadirachta indica—an eco-friendly approach”, Materials Letters, vol. 170, 2016, pp. 175-178.

*Primary Examiner* — Jessica Worsham

(74) *Attorney, Agent, or Firm* — Oblon, McClelland, Maier & Neustadt, L.L.P.

(57) ABSTRACT

A drug delivery system including a zeolitic imidazolate framework-8 (ZIF-8), silica, platinum nanoparticles, and polyethylene glycol. The silica penetrates the pores of the ZIF-8 and at least partially envelopes the ZIF-8 to form a ZIF-8/silica composite. The platinum nanoparticles are present on the surface of the ZIF-8/silica composite, and the polyethylene glycol surrounds the platinum nanoparticles present on the surface of the ZIF-8/silica composite.

19 Claims, 21 Drawing Sheets

DRUG DELIVERY SYSTEM

STATEMENT OF PRIOR DISCLOSURE BY INVENTOR

Aspects of the present disclosure are described in H. G. Alotaibi, E. Al-Abbad, D. Almohazey, V. Ravinayagam, S. Akhtar, H. Dafalla, and B. R. Jermy "Zeolitic Imidazole Framework/Silica Nanocomposite for Targeted Cancer Therapeutics: Comparative Study of Chemo-Drug Cisplatin (CPt) and Green Platinum (GPt) Efficacy"; Int. J. Mol. Sci.; 2024; 25; 3157, incorporated herein by reference in its entirety.

STATEMENT OF ACKNOWLEDGEMENT

The support of the Deanship of Scientific Research at Imam Abdulrahman Bin Faisal University, under grant number 2020-153-DSR, for funding this research work is gratefully acknowledged.

BACKGROUND

Technical Field

The present disclosure is directed towards a drug delivery system, and more particularly, directed towards a drug delivery system including a nanocomposite of zeolitic imidazolate framework-8/silica for delivery of platinum-based drugs.

Description of Related Art

The "background" description provided herein is to present the context of the disclosure generally. Work of the presently named inventors, to the extent it is described in this background section, as well as aspects of the description that may not otherwise qualify as prior art at the time of filing, are neither expressly nor impliedly admitted as prior art against the present invention.

Cancer is one of the world's most feared diseases and is predicted to rise in incidence and mortality by 1% each year until 2030. In general, cancer is caused by uncontrolled cell division that spreads to surrounding tissue, leading to cell death. Chemotherapy drugs are often used to combat the proliferation of cancerous cells, but many have toxic impacts on healthy cells and serious adverse effects, particularly when given at high dosages.

Presently, chemo-drugs such tamoxifen, cisplatin, and anthracyclines (doxorubicin and cyclophosphamide) are used for the treatment of breast cancer. Cisplatin is widely used in various malignancies such as ovarian cancer, testicular cancer, and solid tumors in the head and neck. In addition, around 50% patients are treated with platinum (Pt) compounds. Nevertheless, the drugs are non-specific and induce neurotoxicity, nephrotoxicity, and cytotoxicity to normal cells. Furthermore, low bioavailability and low enhanced permeability and retention reduces treatment efficacy.

To reduce the toxic effect of cisplatin, several Pt complexes including carboplatin and oxaliplatin have been reported. However, such Pt complexes are either toxic or do not match the drug effects of cisplatin. Synthesis of platinum nanoparticles (PtNPs), using green methods is favourable due to the lower toxicity of the metallic Pt form and an environmentally friendly synthesis technique. The yield and morphology of the nanoparticles tends to depend on the plant extract concentrations.

Drug re-purposing technology offers a new pharmacological/therapeutic route for FDA-approved drugs. Several nanocarriers based on polymeric micelles, porous-structured silica, liposomes, dendrimers, polymers, and mesoporous carbon have been reported for targeted cancer therapeutics. Metal organic frameworks (MOFs) are explored for their structural qualities and adsorption properties. MOFs offers high porosity, specific surface area, ease of design, flexibility, and ease of linker modifications for applications in the pharmaceutical industry including adsorption, separation, catalysis, sensing, and drug delivery. Recently, the zeolite imidazole framework (ZIF-8) has been widely used as a drug carrier for biomedical applications. For instance, the attributes of high porosity, easy modification, structural stability, biocompatible metal ions, and low toxicity make it ideal for controlled drug release systems. ZIF-8 nanoparticles are effective pH-responsive drug delivery vehicles, but their small pore size results in low drug loading. Mesoporous nanoparticles like $SiO_2$, ZnO, and Fe offer high drug loading efficiency and controlled release. Combining ZIF-8 with these nanoparticles offers potential for drug loading, controlled release, and monitoring.

Hence, there arises a need for better and efficient drug delivery systems. Therefore, it is one object of the present disclosure to provide a drug delivery system for cancer treatment, that may circumvent the aforementioned drawbacks.

SUMMARY

In an exemplary embodiment, a drug delivery system is described. The drug delivery system includes a zeolitic imidazolate framework-8 (ZIF-8), silica, platinum nanoparticles, and polyethylene glycol. The silica penetrates pores of the ZIF-8 and at least partially envelopes the ZIF-8 to form a ZIF-8/silica composite. The platinum nanoparticles are present on a surface of the ZIF-8/silica composite, and the polyethylene glycol surrounds the platinum nanoparticles present on the surface of the ZIF-8/silica composite.

In some embodiments, particles of the drug delivery system have an average size of 100-200 nm.

In some embodiments, the platinum nanoparticles are spherical.

In some embodiments, the platinum nanoparticles have an average size of 4-10 nm.

In some embodiments, the platinum nanoparticles include $Pt^0$.

In some embodiments, the platinum nanoparticles have a face-centered cubic crystal structure.

In some embodiments, neem extract is bound to a portion of the platinum nanoparticles.

In some embodiments, the platinum nanoparticles form aggregates, and the aggregates have an average size of 50-100 nm.

In some embodiments, the ZIF-8/silica composite has a Brunauer-Emmett-Teller (BET) surface area of 50-100 $m^2/g$, and a pore size of 20-25 nm.

In some embodiments, the silica forms a shell around the ZIF-8 in the ZIF-8/silica composite.

In some embodiments, the drug delivery system includes including C, Pt, Si, Zn, Cl, and O.

In some embodiments, the drug delivery system has a zeta potential of −20 millivolts (mV) to −30 mV.

In some embodiments, the ZIF-8/silica composite has a maximum adsorption capacity for the platinum nanoparticles of 80-100 mg per gram of the ZIF-8/silica composite.

In some embodiments, 80% to 100% of the platinum nanoparticles are released from the drug delivery system in an environment having a pH of 6.6 after 72 hours.

In some embodiments, the drug delivery system has a $EC_{50}$ for human breast cancer cells of 55 micrograms per milliliter (μg/mL) to 65 μg/mL.

In some embodiments, the drug delivery system has an $EC_{50}$ that is lower than an $EC_{50}$ for a same drug delivery system but with cisplatin instead of platinum nanoparticles.

In another exemplary embodiment, a method of making the platinum nanoparticles is described. The method includes forming a powder of neem leaves by mixing the powder of neem leaves in water, heating, and filtering to form an extract; mixing cisplatin in water to form a platinum solution; mixing the platinum solution and the extract for 10-20 hours to form a reaction solution and further separating the platinum nanoparticles from the reaction solution. A portion of the extract is bound to a surface of the platinum nanoparticles, and the platinum nanoparticles are aggregated.

In some embodiments, the platinum nanoparticles are spherical.

In some embodiments, the platinum nanoparticles have an average size of 4-10 nm.

The foregoing general description of the illustrative present disclosure and the following detailed description thereof are merely exemplary aspects of the teachings of this disclosure and are not restrictive.

BRIEF DESCRIPTION OF THE DRAWINGS

A more complete appreciation of this disclosure and many of the attendant advantages thereof will be readily obtained as the same becomes better understood by reference to the following detailed description when considered in connection with the accompanying drawings, wherein.

DETAILED DESCRIPTION

Figure 1A:
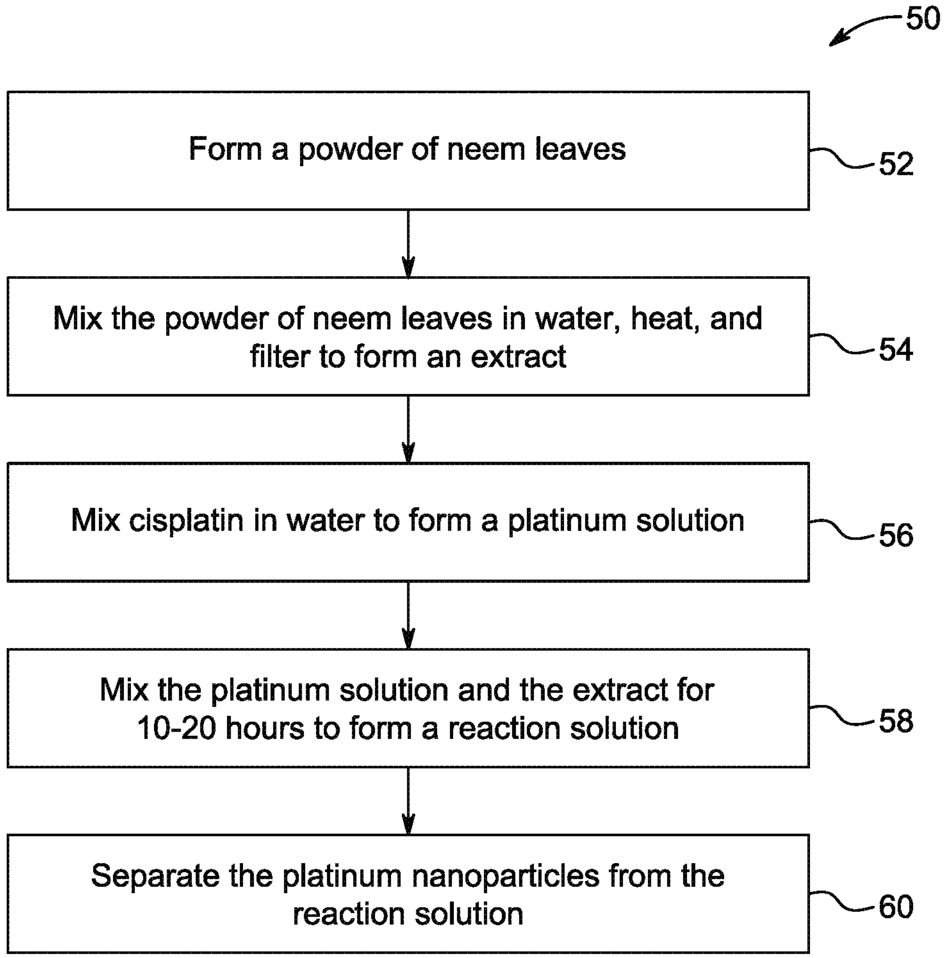
FIG. 1A is a flowchart illustrating a method for preparing platinum nanoparticles (Pt NPs), also referred to as GPt according to certain embodiments.

In the drawings, reference numerals designate identical or corresponding parts throughout the several views. Further, as used herein, the words “a,” “an,” and the like generally carry a meaning of “one or more,” unless stated otherwise.

Where a numerical limit or range is stated herein, the endpoints are included. Also, all values and subranges within a numerical limit or range are specifically included as if explicitly written out.

Furthermore, the terms “approximately,” “approximate,” “about,” and similar terms generally refer to ranges that include the identified value within a margin of 20%, 10%, or preferably 5%, and any values therebetween.

Aspects of the present disclosure are directed towards developing a zeolitic imidazole framework/silica nanocomposite (nanocomposite) to improve the delivery of traditional chemotherapy drugs, preferably platinum containing drugs, during cancer treatment. The present nanocomposite provides performance comparable to cisplatin.

A drug delivery system includes a metal organic framework (MOF). A MOF is a coordination network with organic ligands containing potential voids. A coordination network is a coordination compound extending, through repeating coordination entities, in one dimension, but with cross-links between two or more individual chains, loops, or spiro-links, or a coordination compound extending through repeating coordination entities in two or three dimensions; and finally, a coordination polymer is a coordination compound with repeating coordination entities extending in one, two, or three dimensions. A coordination entity is an ion or neutral molecule that is composed of a central atom, usually that of a metal, to which is attached a surrounding array of atoms or groups of atoms, each of which is called ligands. More succinctly, a metal organic framework is characterized by metal ions or clusters coordinated to organic ligands to form one-, two-, or three-dimensional structures. Typically, a MOF exhibits a regular void or pore structure. The nature of the void or pore structure, including properties or structural factors such as the geometry about the metal ions or clusters, the arrangement of the linkages between metal ions or clusters, and the number, identity, and spatial arrangement of voids or pores. These properties may be described as the structure of the repeat units and the nature of the arrangement of the repeat units. The specific structure of the MOF, which may include the void or pore structure is typically referred to as the MOF topology.

The metal-organic framework comprises a metal ion which is an ion of at least one metal selected from the group consisting of a transition metal (e.g. Sc, Ti, V, Cr, Mn, Fe, Co, Ni, Cu, Y, Zr, Nb, Mo, Tc, Ru, Rh, Pd, Ag, Hf, Ta, W, Re, Os, Ir, Pt, Au, Rf, Db, Sg, Bh, Hs, Mt, Ds, Rg, and Cn), a post-transition metal (e.g. Al, In, Ga, Sn, Bi, Pb, Tl, Zn, Cd, and Hg), and an alkaline earth metal (e.g. Be, Mg, Ca, Sr, Ba, and Ra). Further, these metal ions may be of any oxidation state $M^{+1}$, $M^{+2}$, $M^{+3}$, etc. In one or more embodiments, the metal ion is an ion of at least one metal selected from the group consisting of Zn, Cu, Fe, Ni, Co, Mn, Cr, Cd, Mg, Ca, and Zr.

In the formation of a metal organic framework, the organic ligands must meet certain requirements to form coordination bonds, primarily being multi-dentate, having at least two donor atoms (i.e., N—, and/or O—) and being neutral or anionic. The structure of the metal organic framework is also affected by the shape, length, and functional groups present in the organic linker. In certain embodiments, the metal organic framework of the present disclosure comprises anionic ligands as organic ligands. In one or more embodiments, the organic ligands may have at least two nitrogen donor atoms. For example, the organic ligands may be imidazolate-based, imidazole-derived or ligands similar to an imidazole including, but not limited to, optionally substituted imidazoles, optionally substituted benzimidazoles, optionally substituted imidazolines, optionally substituted pyrazoles, optionally substituted thiazoles, and optionally substituted triazoles.

In one or more embodiments, the ligand may be an imidazole of formula (I) or a benzimidazole of formula (II):

(I)

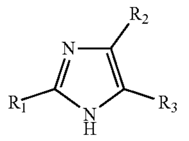

(II)

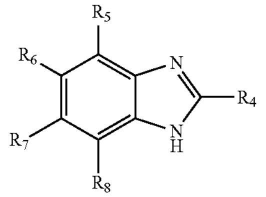

wherein $R_1$, $R_2$, $R_3$, $R_4$, $R_5$, $R_6$, $R_7$, and $R_5$ are each independently selected from the group consisting of a hydrogen, an optionally substituted alkyl, an optionally substituted cycloalkyl, an optionally substituted alkoxy, a hydroxyl, a halogen, a nitro, and a cyano. Preferably, $R_1$, $R_2$, $R_3$, $R_4$, $R_5$, $R_6$, $R_7$, and $R_8$ are each independently a hydrogen, an optionally substituted $C_1$-$C_3$ alkyl group, or an optionally substituted $C_3$-$C_6$ cycloalkyl group. More preferably, $R_1$, $R_2$, $R_3$, $R_4$, $R_5$, $R_6$, $R_7$, and $R_5$ are each independently a hydrogen or a methyl.

Exemplary imidazole-based ligands that may be applicable to the current disclosure include, but are not limited to, imidazole, 2-methylimidazole, 4-methylimidazole, 2-ethylimidazole, 2-isopropylimidazole, 4-tert-butyl-1H-imidazole, 2-ethyl-4-methylimidazole, 2-bromo-1H-imidazole, 4-bromo-1H-imidazole, 2-chloro-1H-imidazole, 2-iodoimidazole, 2-nitroimidazole, 4-nitroimidazole, (1H-imidazol-2-yl) methanol, 4-(hydroxymethyl)imidazole, 2-aminoimidazole, 4-(trifluoromethyl)-1H-imidazole, 4-cyanoimidazole, 3H-imidazole-4-carboxylic acid, 4-imidazolecarboxylic acid, imidazole-2-carboxylic acid, 2-hydroxy-1H-imidazole-4-carboxylic acid, 4,5-imidazoledicarboxylic acid, 5-iodo-2-methyl-1H-imidazole, 2-methyl-4-nitroimidazole, 2-(aminomethyl)imidazole, 4,5-dicyanoimidazole, 4-imidazoleacetic acid, 4-methyl-5-imidazolemethanol, 1-(4-methyl-1H-imidazol-5-yl) methanamine, 4-imidazoleacrylic acid, 5-bromo-2-propyl-1H-imidazole, ethyl-(1H-imidazol-2-ylmethyl)-amine, and 2-butyl-5-hydroxymethylimidazole. In preferred embodiments, the imidazole of formula (I) is 2-methylimidazole.

Exemplary benzimidazole-based ligands that may be applicable to the current disclosure include, but are not limited to, benzimidazole, 5-methylbenzimidazole, 2-methylbenzimidazole, 5-chlorobenzimidazole, 5-bromobenzimidazole, 5,6-dimethylbenzimidazole, 5-methoxybenzimidazole, 2-chlorobenzimidazole, 2-bromo-1H-benzimidazole, 6-bromo-1H-benzimidazole, 5-fluoro-1H-benzimidazole, 5-chloro-2-methylbenzimidazole, methyl benzimidazole-2-acetate, 1H-benzoimidazol-4-ol, 1H-benzimidazol-5-yl-methanol, 2-benzimidazolemethanol, 4-chloro-6-(trifluoromethyl)benzimidazole, 5-chloro-2-(trichloromethyl) benzimidazole, 5-cyanobenzimidazole, (2-benzimidazolyl) acetonitrile, (5-chloro-1H-benzimidazol-2-yl) methanol, 2-(chloromethyl)benzimidazole, 5-iodo-2-methylbenzimidazole, (5-chloro-1H-benzimidazol-2-yl)methylamine, 2-(aminomethyl)benzimidazole, 2-(6-chloro-1H-benzimidazol-2-yl) ethanol, 2-(1H-benzoimidazol-2-yl)-acetamide, (6-methoxy-1H-benzimidazol-2-yl) methanol, 5,6-dimethoxybenzimidazole, 2-(1H-benzoimidazol-2-yl)-ethylamine, 1-(5-methyl-1H-benzimidazol-2-yl) methanamine, 1-(5-methyl-1H-benzimidazol-2-yl) ethanamine, 2-benzimidazolepropionic acid, 2-(5-methyl-1H-benzimidazol-2-yl) ethanamine, 2-(3-hydroxy-N-propyl)-5-(trifluoromethyl)-benzimidazole, and N-methyl-1-(5-methyl-1H-benzimidazol-2-yl) methanamine.

Metal organic frameworks comprising such imidazole or benzimidazole ligands are typically referred to as zeolitic imidazolate frameworks (ZIFs). In some embodiments, the metal organic framework is a zeolitic imidazolate framework. Examples of suitable metal organic frameworks include, but are not limited to isoreticular metal organic framework-3 (IRMOF-3), MOF-69A, MOF-69B, MOF-69C, MOF-70, MOF-71, MOF-73, MOF-74, MOF-75, MOF-76, MOF-77, MOF-78, MOF-79, MOF-80, DMOF-1-$NH_2$, UMCM-1-$NH_2$, MOF-69-80, ZIF-1, ZIF-2, ZIF-3, ZIF-4, ZIF-5, ZIF-6, ZIF-7, ZIF-8, ZIF-9, ZIF-10, ZIF-11, ZIF-12, ZIF-14, ZIF-20, ZIF-21, ZIF-22, ZIF-23, ZIF-25, ZIF-60, ZIF-61, ZIF-62, ZIF-63, ZIF-64, ZIF-65, ZIF-66, ZIF-67, ZIF-68, ZIF-69, ZIF-70, ZIF-71, ZIF-72, ZIF-73, ZIF-74, ZIF-75, ZIF-76, ZIF-77, ZIF-78, ZIF-79, ZIF-80, ZIF-81, ZIF-82, ZIF-90, ZIF-91, ZIF-92, ZIF-93, ZIF-94, ZIF-96, ZIF-97, ZIF-100, ZIF-108, ZIF-303, ZIF-360, ZIF-365, ZIF-376, ZIF-386, ZIF-408, ZIF-410, ZIF-412, ZIF-413, ZIF-414, ZIF-486, ZIF-516, ZIF-586, ZIF-615, and ZIF-725. In a most preferred embodiment, the ZIF is ZIF-8 in which the imidazole ligand is 2-methylimidazole and the metal ion is Zn.

The drug delivery system further includes silica ($SiO_2$). In some embodiments, the silica at least partially envelopes the ZIF-8, preferably 50%, 60%, 70%, 80%, 90%, or 100% of the ZIF-8 is enveloped by the silica to form a ZIF-8/silica composite, where the 100% is the formation of a shell around the ZIF-8. In some embodiments, the silica forms a shell around the ZIF-8 in the ZIF-8/silica composite.

The silica penetrates the pores of the ZIF-8 to form a ZIF-8/silica composite. The silica forms a shell around the ZIF-8 in the ZIF-8/silica composite, while the ZIF-8 forms the core in the ZIF-8/silica composite. The particles of the ZIF-8/silica composite have an average size of 100-500 nm, preferably 150-450 nm, 200-400 nm, or 250-300 nm. The ZIF-8/silica composite has BET surface area of 50-100 meter square per gram ($m^2/g$), more preferably 70-80 $m^2/g$, and yet more preferably 75 $m^2/g$. In some embodiments, the ZIF-8/silica composite has only mesopores (2-50 nm) and no micropores (less than 2 nm). In some embodiments, the ZIF-8/silica composite has an average pore size of 20-25 nm, preferably 21-24 nm, or 22-23 nm. In some embodiments, the ZIF-8/silica composite has a dual pore size distribution with mesopores from 15-20 nm, preferably 16-19 nm, or 17-18 nm, and 35-40 nm, preferably 36-39 nm, or 37-38 nm, respectively. In some embodiments, the ZIF-8/silica composite has an average pore size that is at least 10× greater than that of the ZIF-8 alone.

The drug delivery system further includes platinum nanoparticles. In some embodiments, the platinum nanoparticles are present on the surface and/or in pores of the ZIF-8/silica composite. The platinum nanoparticles can be any morphology such as nanospheres, nanowires, nanocrystals, nanosheets, nanorectangles, nanotriangles, nanopentagons, nanohexagons, nanoprisms, nanodisks, nanocubes, nanoribbons, nanoblocks, nanobeads, nanotoroids, nanodiscs, nanobarrels, nanogranules, nanowhiskers, nanoflakes, nanofoils, nanopowders, nanoboxes, nanostars, tetrapods, nanobelts, nano-urchins, nanoflowers, etc., and mixtures thereof. In a preferred embodiment, the platinum nanoparticles are in a form of spheres. In some embodiments, the platinum nanoparticles have an average size of 4-10 nm, more preferably 5, 6, 7, 8, or 9 nm.

In a preferred embodiment, the platinum nanoparticles are made by a green method as will be described later. Cisplatin is used as a source of platinum nanoparticles, optionally in some embodiments, other platinum-based drugs such as carboplatin, oxaliplatin, nedaplatin, triplatin tetranitrate, phenanthriplatin, and picoplatin; satraplatin may be used independently/in combination with cisplatin as a source for the platinum, nanoparticles. The platinum nanoparticles made by the green method then require a reducing agent for the platinum source. The reducing agent is preferably derived from a plant, preferably a neem plant or a neem extract. The neem extract reduces platinum-based drugs, preferably cisplatin, to platinum nanoparticles. In some embodiments, the platinum source includes $Pt^2$, $Pt^4$, and/or $Pt^6$. In some embodiments, in the method of making the platinum is reduced to $Pt^0$, thus the platinum nanoparticles include $Pt^0$.

In a preferred embodiment, neem extract is bound to a portion of the platinum nanoparticles, preferably 50%, 60%, 70%, 80%, 90%, or 100% of the platinum nanoparticles. In some embodiments, the components of the neem extract bound to the platinum nanoparticles are cellulose or phytochemicals such as but not limited to carotenoids and polyphenols, which include phenolic acids, flavonoids, stilbenes or lignans.

In some embodiments, platinum nanoparticles have a triclinic, monoclinic, orthorhombic, tetragonal, trigonal, hexagonal, or cubic crystal structure. In some embodiments, platinum nanoparticles have a face-centered cubic crystal structure. In some embodiments, the platinum nanoparticles may have a body-centered cubic structure (BCC), a face-centered cubic structure (FCC), or both. The platinum nanoparticles form aggregates and the aggregates have an average size of 50-100 nm, preferably 60-90 nm, or 70-80 nm. In some embodiments, the aggregation is due to the presence of the neem extract on the platinum nanoparticles.

The ZIF-8/silica composite has a maximum adsorption capacity for the platinum nanoparticles of 80-100 mg per gram (mg/g), more preferably 88 to 92 mg/g, and yet more preferably 90.9 mg/g of the ZIF-8/silica composite. In other words, the ZIF-8/silica composite can hold 80-100 mg of the platinum nanoparticles for delivery.

The drug delivery system further optionally includes a coating such as but not limited to polyethylene glycol and chitosan, which surrounds the platinum nanoparticles present on the surface of the ZIF-8/silica composite. In some embodiments, the polyethylene glycol surrounds at least 50%, preferably 60%, 70%, 80%, 90%, or 100% of the ZIF-8/silica composite with the platinum nanoparticles. The inclusion of the platinum nanoparticles, the ZIF-8, the silica composite and the polyethylene glycol together form the drug delivery system. In a preferred embodiment, none of the components in the drug delivery system interact through covalent bonds, rather through weak interactions such as hydrogen bonds, van der Waals interactions, ionic bonds, and hydrophobic bonds.

The particles of the drug delivery system can be any morphology such as nanospheres, nanowires, nanocrystals, nanosheets, nanorectangles, nanotriangles, nanopentagons, nanohexagons, nanoprisms, nanodisks, nanocubes, nanoribbons, nanoblocks, nanobeads, nanotoroids, nanodiscs, nanobarrels, nanogranules, nanowhiskers, nanoflakes, nanofoils, nanopowders, nanoboxes, nanostars, tetrapods, nanobelts, nano-urchins, nanoflowers, etc., and mixtures thereof. In a preferred embodiment, the particles of the drug delivery system are in a form of spheres. In some embodiments, particles of the drug delivery system have an average size of 100-200 nm, preferably 125-175 nm or 140-160 nm. In some embodiments, the drug delivery system includes C, Pt, Si, Zn, Cl, and O. In some embodiments, the drug delivery system has a zeta potential of −20 millivolts (mV) to −30 mV, preferably −22 to −28 mV, - or −24 to −26 mV.

In some embodiments, the drug delivery system is used to treat cancer. As used herein, the term "cancer" refers to all types of cancer, neoplasm or malignant tumors found in mammals (e.g., humans), including leukemias, lymphomas, carcinomas, and sarcomas. Exemplary cancers that may be treated with a compound or method provided herein include brain cancer, glioma, glioblastoma, neuroblastoma, prostate cancer, colorectal cancer, pancreatic cancer, Medulloblastoma, melanoma, cervical cancer, gastric cancer, ovarian cancer, lung cancer, cancer of the head, Hodgkin's Disease, and Non-Hodgkin's Lymphomas. Exemplary cancers that may be treated with a compound or method provided herein include cancer of the thyroid, endocrine system, brain, breast, cervix, colon, head & neck, liver, kidney, lung, ovary, pancreas, rectum, stomach, and uterus. Additional examples include, thyroid carcinoma, cholangiocarcinoma, pancreatic adenocarcinoma, skin cutaneous melanoma, colon adenocarcinoma, rectum adenocarcinoma, stomach adenocarcinoma, esophageal carcinoma, head and neck squamous cell carcinoma, breast invasive carcinoma, lung adenocarcinoma, lung squamous cell carcinoma, non-small cell lung carcinoma, mesothelioma, multiple myeloma, neuroblastoma, glioma, glioblastoma multiforme, ovarian cancer, rhabdomyosarcoma, primary thrombocytosis, primary macroglobulinemia, primary brain tumors, malignant pancreatic insulanoma, malignant carcinoid, urinary bladder cancer, premalignant skin lesions, testicular cancer, thyroid cancer, neuroblastoma, esophageal cancer, genitourinary tract cancer, malignant hypercalcemia, endometrial cancer, adrenal cortical cancer, neoplasms of the endocrine or exocrine pancreas, medullary thyroid cancer, medullary thyroid carcinoma, melanoma, colorectal cancer, papillary thyroid cancer, hepatocellular carcinoma, or prostate cancer.

In some embodiments, the drug delivery system includes a pharmaceutically acceptable excipient (excipient), which, as used herein, includes any and all solvents, dispersion media, diluents, or other liquid vehicles, dispersion or suspension aids, surface active agents, isotonic agents, thickening or emulsifying agents, preservatives, solid binders, lubricants and the like, as suited to the particular dosage form desired.

In some embodiments, the pharmaceutically acceptable excipient is at least 95%, 96%, 97%, 98%, 99%, or 100% pure. In some embodiments, the excipient is approved for use in humans and for veterinary use. In some embodiments, the excipient is approved by United States Food and Drug Administration. In some embodiments, the excipient is pharmaceutical grade. In some embodiments, the excipient meets the standards of the United States Pharmacopoeia (USP), the European Pharmacopoeia (EP), the British Pharmacopoeia, and/or the International Pharmacopoeia.

Pharmaceutically acceptable excipients used in the manufacture of pharmaceutical compositions include, but are not limited to, inert diluents, dispersing and/or granulating agents, surface active agents and/or emulsifiers, disintegrating agents, binding agents, preservatives, buffering agents, lubricating agents, and/or oils. Exemplary diluents include, but are not limited to, calcium carbonate, sodium carbonate, calcium phosphate, dicalcium phosphate, calcium sulfate, calcium hydrogen phosphate, sodium phosphate lactose, sucrose, cellulose, microcrystalline cellulose, kaolin, mannitol, sorbitol, inositol, sodium chloride, dry starch, cornstarch, powdered sugar, etc., and combinations thereof.

Exemplary granulating and/or dispersing agents include, but are not limited to, potato starch, corn starch, tapioca starch, sodium starch glycolate, clays, alginic acid, guar gum, citrus pulp, agar, bentonite, cellulose and wood products, natural sponge, cation-exchange resins, calcium carbonate, silicates, sodium carbonate, cross-linked polyvinylpyrrolidone) (crospovidone), sodium carboxymethyl starch (sodium starch glycolate), carboxymethyl cellulose, cross-linked sodium carboxymethyl cellulose (croscarmellose), methylcellulose, pregelatinized starch (starch 1500), microcrystalline starch, water-insoluble starch, calcium carboxymethyl cellulose, magnesium aluminum silicate (Veegum), sodium lauryl sulfate, quaternary ammonium compounds, etc., and combinations thereof.

Exemplary surface active agents and/or emulsifiers include, but are not limited to, natural emulsifiers (e.g. acacia, agar, alginic acid, sodium alginate, tragacanth, chondrux, cholesterol, xanthan, pectin, gelatin, egg yolk, casein, wool fat, cholesterol, wax, and lecithin), colloidal clays (e.g. bentonite (aluminum silicate) and Veegum (magnesium aluminum silicate)), long chain amino acid derivatives, high molecular weight alcohols (e.g. stearyl alcohol, cetyl alcohol, oleyl alcohol, triacetin monostearate, ethylene glycol distearate, glyceryl monostearate, and propylene glycol monostearate, polyvinyl alcohol), carbomers (e.g. carboxy polymethylene, polyacrylic acid, acrylic acid polymer, and carboxyvinyl polymer), carrageenan, cellulosic derivatives (e.g. carboxymethylcellulose sodium, powdered cellulose, hydroxymethyl cellulose, hydroxypropyl cellulose, hydroxypropyl methylcellulose, methylcellulose), sorbitan fatty acid esters (e.g. polyoxyethylene sorbitan monolaurate (Tween 20), polyoxyethylene sorbitan (Tween 60), polyoxyethylene sorbitan monooleate (Tween 80), sorbitan monopalmitate (Span 40), sorbitan monostearate (Span 60), sorbitan tristearate (Span 65), glyceryl monooleate, sorbitan monooleate (Span 80)), polyoxyethylene esters (e.g. polyoxyethylene monostearate ((Myrj 45), polyoxyethylene hydrogenated castor oil, polyethoxylated castor oil, polyoxymethylene stearate, and Solutol), sucrose fatty acid esters, polyethylene glycol fatty acid esters (e.g. Cremophor), polyoxyethylene ethers, (e.g. polyoxyethylene lauryl ether (Brij 30)), poly(vinyl-pyrrolidone), diethylene glycol monolaurate, triethanolamine oleate, sodium oleate, potassium oleate, ethyl oleate, oleic acid, ethyl laurate, sodium lauryl sulfate, Pluronic F 68, Poloxamer 188, cetrimonium bromide, cetylpyridinium chloride, benzalkonium chloride, docusate sodium, etc. and/or combinations thereof.

Exemplary binding agents include, but are not limited to, starch (e.g. cornstarch and starch paste); gelatin; sugars (e.g.

sucrose, glucose, dextrose, dextrin, molasses, lactose, lactitol, mannitol,); natural and synthetic gums (e.g. acacia, sodium alginate, extract of Irish moss, panwar gum, ghatti gum, mucilage of isapol husks, carboxymethylcellulose, methylcellulose, ethylcellulose, hydroxyethylcellulose, hydroxypropyl cellulose, hydroxypropyl methylcellulose, microcrystalline cellulose, cellulose acetate, polyvinylpyrrolidone), magnesium aluminum silicate (Veegum), and larch arabogalactan); alginates; polyethylene oxide; polyethylene glycol; inorganic calcium salts; silicic acid; polymethacrylates; waxes; water; alcohol; etc.; and combinations thereof.

Exemplary preservatives may include antioxidants, chelating agents, antimicrobial preservatives, antifungal preservatives, alcohol preservatives, acidic preservatives, and other preservatives. Exemplary antioxidants include, but are not limited to, alpha tocopherol, ascorbic acid, acorbyl palmitate, butylated hydroxyanisole, butylated hydroxytoluene, monothioglycerol, potassium metabisulfite, propionic acid, propyl gallate, sodium ascorbate, sodium bisulfite, sodium metabisulfite, and sodium sulfite.

Exemplary chelating agents include ethylenediaminetetraacetic acid (EDTA), citric acid monohydrate, disodium edetate, dipotassium edetate, edetic acid, fumaric acid, malic acid, phosphoric acid, sodium edetate, tartaric acid, and trisodium edetate. Exemplary antimicrobial preservatives include, but are not limited to, benzalkonium chloride, benzethonium chloride, benzyl alcohol, bronopol, cetrimide, cetylpyridinium chloride, chlorhexidine, chlorobutanol, chlorocresol, chloroxylenol, cresol, ethyl alcohol, glycerin, hexetidine, imidurea, phenol, phenoxyethanol, phenylethyl alcohol, phenylmercuric nitrate, propylene glycol, and thimerosal. Exemplary antifungal preservatives include, but are not limited to, butyl paraben, methyl paraben, ethyl paraben, propyl paraben, benzoic acid, hydroxybenzoic acid, potassium benzoate, potassium sorbate, sodium benzoate, sodium propionate, and sorbic acid. Exemplary alcohol preservatives include, but are not limited to, ethanol, polyethylene glycol, phenol, phenolic compounds, bisphenol, chlorobutanol, hydroxybenzoate, and phenylethyl alcohol. Exemplary acidic preservatives include, but are not limited to, vitamin A, vitamin C, vitamin E, beta-carotene, citric acid, acetic acid, dehydroacetic acid, ascorbic acid, sorbic acid, and phytic acid. Other preservatives include, but are not limited to, tocopherol, tocopherol acetate, deteroxime mesylate, cetrimide, butylated hydroxyanisol (BHA), butylated hydroxytoluened (BHT), ethylenediamine, sodium lauryl sulfate (SLS), sodium lauryl ether sulfate (SLES), sodium bisulfite, sodium metabisulfite, potassium sulfite, potassium metabisulfite, Glydant Plus, Phenonip, methylparaben, Germall 115, Germaben II, Neolone, Kathon, and Euxyl. In certain embodiments, the preservative is an antioxidant. In other embodiments, the preservative is a chelating agent.

Exemplary buffering agents include, but are not limited to, citrate buffer solutions, acetate buffer solutions, phosphate buffer solutions, ammonium chloride, calcium carbonate, calcium chloride, calcium citrate, calcium glubionate, calcium gluceptate, calcium gluconate, D-gluconic acid, calcium glycerophosphate, calcium lactate, propanoic acid, calcium levulinate, pentanoic acid, dibasic calcium phosphate, phosphoric acid, tribasic calcium phosphate, calcium hydroxide phosphate, potassium acetate, potassium chloride, potassium gluconate, potassium mixtures, dibasic potassium phosphate, monobasic potassium phosphate, potassium phosphate mixtures, sodium acetate, sodium bicarbonate, sodium chloride, sodium citrate, sodium lactate, dibasic sodium phosphate, monobasic sodium phosphate, sodium phosphate mixtures, tromethamine, magnesium hydroxide, aluminum hydroxide, alginic acid, pyrogen-free water, isotonic saline, Ringer's solution, ethyl alcohol, etc., and combinations thereof.

Exemplary lubricating agents include, but are not limited to, magnesium stearate, calcium stearate, stearic acid, silica, talc, malt, glyceryl behanate, hydrogenated vegetable oils, polyethylene glycol, sodium benzoate, sodium acetate, sodium chloride, leucine, magnesium lauryl sulfate, sodium lauryl sulfate, etc., and combinations thereof. Exemplary oils include, but are not limited to, almond, apricot kernel, avocado, babassu, bergamot, black current seed, borage, cade, camomile, canola, caraway, carnauba, castor, cinnamon, cocoa butter, coconut, cod liver, coffee, corn, cotton seed, emu, eucalyptus, evening primrose, fish, flaxseed, geraniol, gourd, grape seed, hazel nut, hyssop, isopropyl myristate, jojoba, kukui nut, lavandin, lavender, lemon, litsea cubeba, macademia nut, mallow, mango seed, meadowfoam seed, mink, nutmeg, olive, orange, orange roughy, palm, palm kernel, peach kernel, peanut, poppy seed, pumpkin seed, rapeseed, rice bran, rosemary, safflower, sandalwood, sasquana, savoury, sea buckthorn, sesame, shea butter, silicone, soybean, sunflower, tea tree, thistle, tsubaki, vetiver, walnut, and wheat germ oils. Exemplary oils include, but are not limited to, butyl stearate, caprylic triglyceride, capric triglyceride, cyclomethicone, diethyl sebacate, dimethicone 360, isopropyl myristate, mineral oil, octyldodecanol, oleyl alcohol, silicone oil, and combinations thereof.

The drug delivery system may be formulated for oral and parenteral administration, including, but not limited to, pharmaceutically acceptable emulsions, microemulsions, solutions, suspensions, syrups, and elixirs. In order to prolong the effect of a drug, it is often desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

In a preferred embodiment, 80-100%, preferably 85-95% or 90-93% of the platinum nanoparticles are released from the drug delivery system in an environment having a pH of 6.6 after 72 hours. These conditions are meant to simulate the pH of a tumor (6.6) environment in a subject. In a preferred embodiment, 30-50%, preferably 35-45% or 40-43% of the platinum nanoparticles are released from the drug delivery system in an environment having a pH of 7.4 after 72 hours. These conditions are meant to simulate the pH of a normal physiological (7.4) environment in a subject. In a preferred embodiment, the percentage of platinum nanoparticles released from the drug delivery system is higher at a pH of 6.6 than a pH of 7.4, thus the drug delivery system selectively releases the platinum nanoparticles at a pH of 6.6, i.e., a tumor environment.

The drug delivery system has a half maximal effective concentration ($EC_{50}$) for human breast cancer cells of 55-65 μg/mL, preferably 57-63 μg/mL, or 59-61 μg/mL. As used herein, the term 'half maximal effective concentration ($EC_{50}$)' refers to the concentration of a drug, antibody, or toxicant that induces a biological response halfway between the baseline and maximum after a specified exposure time. The drug delivery system has an $EC_{50}$ that is lower than an $EC_{50}$ for the same drug delivery system but with cisplatin instead of platinum nanoparticles. Thus, the drug delivery system is as effective or more effective against cancer cells than cisplatin. The components of the drug delivery system form a synergistic relationship to provide improved performance.

FIG. 1 illustrates a schematic flow chart of a method 50 of preparing the platinum nanoparticles. The order in which the method 50 is described is not intended to be construed as a limitation, and any number of the described method steps can be combined in any order to implement the method 50. Additionally, individual steps may be removed or skipped from the method 50 without departing from the spirit and scope of the present disclosure.

At step 52, the method 50 includes forming a powder of neem leaves. In some embodiments, neem leaves may be substituted by other parts of the neem plant, such as root, stem, flowers, seeds, or a combination thereof. In some embodiments, other herbs/plants that act as a reducing agent may be used as well. The powder may be obtained by grinding the nee leaves/any part of a neem plant using a grinder/mixer.

At step 54, the method 50 includes mixing the powder of neem leaves in water, heating, and filtering to form an extract. In some embodiments, water may be tap water, distilled water, bi-distilled water, deionized water, deionized distilled water, reverse osmosis water, hard water, fresh water, brine/salt water, the hard water, and the freshwater may include salts of sodium, magnesium, calcium, potassium, ammonium, and iron, and anions such as chloride, bicarbonate, carbonate, sulfate, sulfite, phosphate, iodide, nitrate, acetate, citrate, fluoride, and nitrite. In a preferred embodiment, water is distilled water. The concentration of powder in water is around 1-10%, preferably 5%. After mixing the powder in water, the powder is heated using heating appliances such as ovens, microwaves, autoclaves, hot plates, heating mantles and tapes, oil baths, salt baths, sand baths, air baths, hot-tube furnaces, flasks, and hot-air guns to a temperature of 70-100° C., preferably 90° C., for 20-60 minutes, preferably 30 minutes, to form a suspension. The suspension is further filtered to obtain an extract. In some embodiments, the extract may be obtained by any other methods known in the art (organic solvent extraction).

At step 56, the method 50 includes mixing cisplatin in water to form a platinum solution. The concentration of cisplatin in the platinum solution is in the range of 0.1 to 5 mM, preferably 0.5 to 2 mM, preferably 0.8 to 1.2 mM, preferably 1 mM. Cisplatin is used as a source of platinum, optionally in some embodiments, other platinum-based drugs such as carboplatin, oxaliplatin, nedaplatin, triplatin tetranitrate, phenanthriplatin, picoplatin, satraplatin may be used independently/in combination with cisplatin to form the platinum solution. The concentration of the platinum-based drugs in the platinum solution may be beyond the ranges described as well, based on the choice of the platinum-based drug. The cisplatin is mixed in water via stirring, swirling, or a combination thereof, to form the platinum solution.

At step 58, the method 50 includes mixing the platinum solution and the extract for 10-20 hours, preferably 12-14 hours to form a reaction solution. The v/v ratio of the platinum solution to the extract is in the range of 15:1-1:1, including 1:1, 2:1, 3:1, 4:1, 5:1, 6:1, 7:1, 8:1, 9:1, 10:1, 11:1, 12:1, 13:1, 14:1, 15:1, and most preferably about 9:1. The extract reduces the platinum-based drug in the platinum solution the reaction solution to form platinum nanoparticles. The platinum nanoparticles have morphological properties are previously described.

At step 60, the method 50 includes separating the platinum nanoparticles from the reaction solution. In a preferred embodiment, separation takes place by gradual heating to a temperature range of 40-150° C. for 1-5 hours, preferably 3 hours.

EXAMPLES

The following examples demonstrate a drug delivery system. The examples are provided solely for illustration and are not to be construed as limitations of the present disclosure, as many variations thereof are possible without departing from the spirit and scope of the present disclosure.

Example 1: Materials and Methods

ZIF-8 (Basolite Z1200), Tetraethyl orthosilicate (reagent grade, 98%), ammonia (25%, Suprapur), sulfuric acid (ACS reagent, 95-98%), methanol (ACS reagent, 99.8%), ethanol (BioUltra, 99.8%), and polyethylene glycol (Mwt~400) were purchased from Sigma Aldrich, St. Louis, MO, USA.

Example 2: PtNP Synthesis

Neem leaves were purchased from the local herbal market in Saudi Arabia. Aqueous extracts of neem leaves were prepared by dissolving 5 g of neem leaf powder in 100 mL of distilled water in an Erlenmeyer flask and boiled at 90° C. for 30 min. Then, the suspension was filtered through Whatman No. 1 filter paper and preserved at 4° C. Cisplatin solution (1 mM) was prepared and used as a source for platinum, while neem leaf extract acts as a reducing agent. After the preparation of solution mixtures, 20 mL of neem leaf extract solution was added to 180 mL of metal solution dropwise, stirred for 1 h, and kept stationary overnight. After adding leaf extract, the color changed from green to brown. The sample was recovered by gradually heating the solution from 40° C. to 150° C. for 3 h.

Example 3: ZIF-8/Silica

The zeolitic imidazolate framework (1 g) was dissolved in 50 mL of deionized water and 50 mL of ethanol and stirred for 10 min. Then, silica source TEOS (5 mL) and 12 mL of $NH_3$ solution (25%) were added to the ZIF-8 mixture at pH ~9 and stirred for 2 h. The solution was centrifuged, washed twice, and placed in the oven at 90° C. and dried overnight.

Example 4: ZIF-8/Silica/Pt/PEG

The Pt complex (CPt and GPt) (30 mg) was functionalized with ZIF-8/silica (600 mg), corresponding to a ratio of 0.05, by stirring under a normal saline solution. The amount of Pt complex present in the sample was calculated based on the Pt present in the collected filter-ant solution along with washing (5 mL) using UVvisible spectroscopy. The entrapment efficiency (EE %) and the loading capacity (LC %) of the two formulations (cisplatin and green Pt) were calculated using the following formula:

$$(EE\ \%) = \left(\frac{Pt \text{ in } ZIF\text{-}8/\text{silica}}{\text{Initial } Pt}\right) \times 100\%$$

-continued $$(LC\ \%) = \left(\frac{\text{Initial amount of } Pt\text{−supernatant } Pt}{ZIF\text{−8/silica}}\right) \times 100$$

Figure 11:
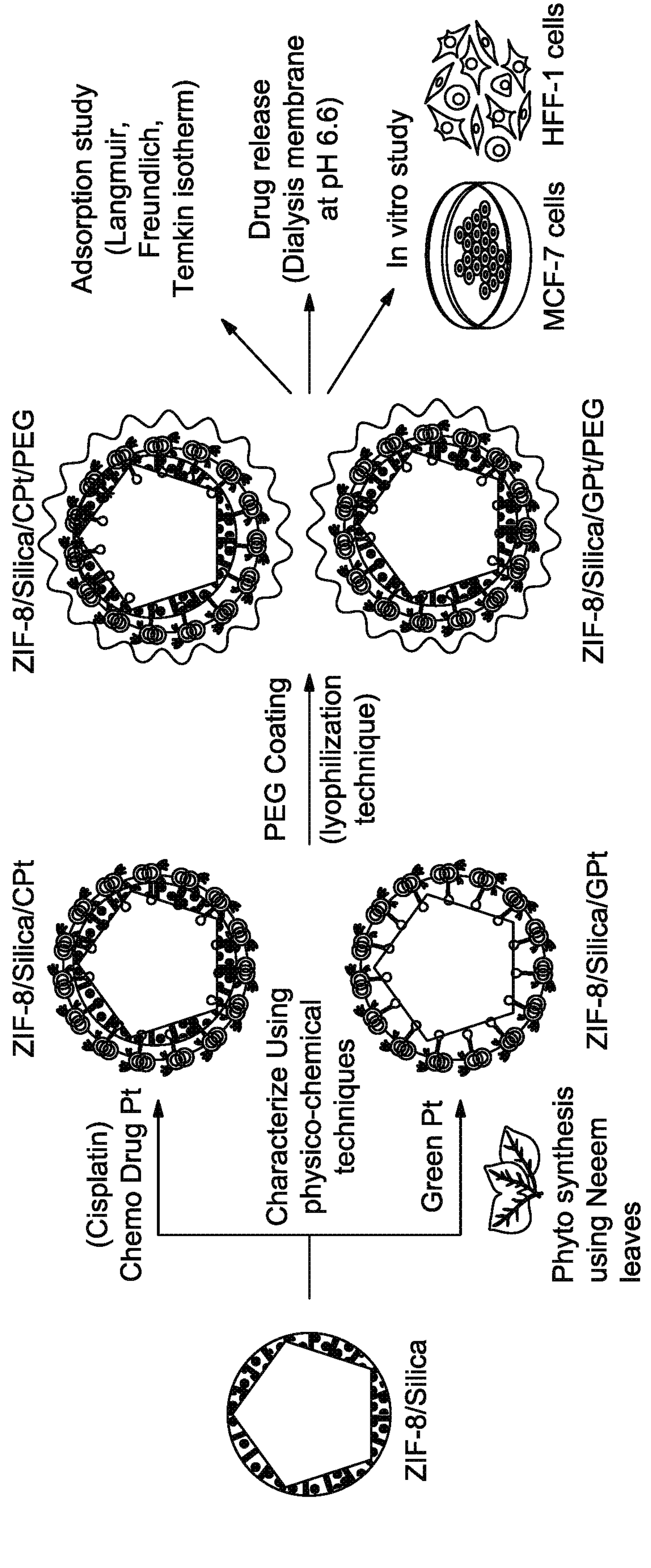
FIG. 11 is a schematic illustration of ZIF-8/silica composite formation, GPT functionalization, CPt functionalization, followed by PEG coating for potential targeted cancer therapeutics, according to certain embodiments.

The final Pt complex in the nanocarrier was about 27.2 mg. The calculation revealed that ZIF-8/silica with cisplatin had an EE of 91% and LC of 4.54%, while GPt showed an EE of 86% with LC of 4.31%. After drug functionalization, both nano-formulations were pegylated using the lyophilization technique. In this step, liquid solution PEG with a molecular weight of 400 (14 μL) was mixed in distilled water (3 mL). Further, 150 mg of the sample, including ZIF-8/Silica/CPt or ZIF-8/Silica/GPt, was added and stirred overnight. Furthermore, the sample was lyophilized, recovered, and stored at 4° C. Each composite throughout is labelled using "/" to separate each component in the composite, where GPt are the Pt nanoparticles synthesized with neem leaves and CPt or Cp is cisplatin. A depiction of the ZIF-8/silica/GPt/PEG and the ZIF-8/silica/CPt/PEG nanocomposites are shown in FIG. 11.

Example 5: Characterization Techniques

The structural transformations of the crystalline phase of ZIF-8 upon nanocomposite formation with silica and green Pt were analyzed and confirmed via powdered X-ray diffraction (XRD) technique in the Miniflex 600, Rigaku, Japan. ZIF-8 and nanocomposite textural variations were measured using the nitrogen adsorption technique (ASAP-2020 plus, Micromeritics, Norcross, GA, USA). About 20 mg of the sample was placed into the sample cell. Prior to surface area analysis, the sample moisture was removed by pretreatment at 50° C. for 2 h under a vacuum. The chemical states of green-synthesized Pt NPs, nanocarrier, and nano-formulations were measured using DRS-UV-visible spectroscopy analysis (JASCO, Tokyo, Japan). The degradation patterns of ZIF-8, ZIF-8/silica, and nano-formulations were measured using thermogravimetric analysis and differential thermal analysis (TGA-DTA) by the STA 6000, Perkin Elmer, USA. The zeta potential of Pt and nanocomposites was analysed using Zetasizer Nano ZS. About 5 mg of nano-formulation was sonicated (30 min) in 10 mL of phosphate-buffered saline (PBS) solution (pH 7.4). For analysis, the sample was transferred into a quartz glass cell and measured. The pegylated samples were dried using an automated freeze dryer Lyovapor L-200. SEM-EDS of the selected sample ZIF-8/silica/GPt was characterized using JSM-6610LV. Elemental mapping was obtained by energy dispersive spectroscopy (EDS) using Aztec Version 4.0 software. The morphology of ZIF-8, ZIF-8/silica, green Pt, ZIF-8/Silica/CPt, and ZIF-8/Silica/GPt was analysed using transmission electron microscopy (JEM2100F from JEOL Ltd., Tokyo, Japan). The lattice fringes were measured using Gatan digital micrograph software (version 1.84.1282).

Example 6: Adsorption Study

The isothermal behaviour of drug adsorption was investigated using isotherm models like Langmuir, Freundlich, and Temkin isotherm. In the first step, 200 ppm of cisplatin or green platinum stock solution (S.S (1)) was prepared by dissolving 50 mg of source in 50 mL of release media (pH 6.6). Then, different ppm solutions (2 ppm to 8 ppm) were prepared. For adsorption, 10 mL of each ppm solution was added to a conical flask, 100 mg of ZIF-8/silica was added, and the adsorption study was performed for 20 h in a shaker. The shaking was maintained at 50 rpm. After that, the solution mixture was filtered, and the supernatant was analysed for platinum concentration using inductively coupled plasma spectroscopy (ICP).

The formula for adsorption is as follows:

$$Q_p = (C_0 - C_e)V/W$$

where $C_e$ is the unloaded amount at equilibrium conditions in mg/L, $C_0$ is the initial concentration in mg/L, V is the volume of solution in liters, and W is the weight of adsorbent ZIF-8/silica in grams.

The formula for the removal capacity Q (mg/g) at varying contact times is as follows:

$$Q_t = (C_0 - C_e)V/W$$

The aforementioned symbols refer to the same parameters as the formula for adsorption.

Example 7: Drug Release Study

The release profile of ZIF-8/silica/CPt/PEG and ZIF-8/Silica/GPt/PEG nano-formulations was studied using a dialysis membrane technique. Prior to the study, the membrane was activated by placing it in normal saline at 37° C. under a magnetic stirrer. After that, 15 mg of sample was dispersed inside the membrane and placed in a 25 mL beaker (pH 6.6). The tumor acidic pH solution of 6.6 was prepared by dissolving each vial of pellets (P8165, Sigma-Aldrich) in 3.8 L of distilled water. In the case of a normal pH of 7.4, the pH of the solution was maintained using tablets of phosphate-buffered saline (P4417, Sigma-Aldrich). Periodically, at different time intervals (0.25, 0.5, 0.7, 1, 2, 3, 4, 5, 6, 12, 24, 48, and 72 h), 5 mL of solution was withdrawn, replaced with fresh normal saline, and the contents were analyzed for Pt content using UV-visible spectroscopy.

Example 8: In-Vitro Study

The cytotoxic efficiency of the nanocomposites with green cisplatin was compared to that of nanocomposites prepared with commercially available cisplatin. The cytotoxicity was conducted using the following cell lines: human mammary adenocarcinoma cell line (MCF7) and human foreskin fibroblasts (HFFs). Cell lines were purchased from ATCC (American Type Culture Collection), United States. Cells were cultured in DMEM, 10% HI-FBS, 1% penicillin-streptomycin, and 1% MEM-NEAA. Cultures were incubated at 37° C. and 5% $CO_2$ under humidified conditions. For the cytotoxicity assay, cells were cultured in a 96-well plate at 20,000 cells/well. All cell culture reagents were purchased from Thermo Fisher Scientific, USA.

Example 9: Cell Treatment

Cells were treated for 48 h under the following conditions: ZIF-8/silica, ZIF-8/silica/Cp, ZIF-8/silica/GPt, GPt, ZIF-8/silica/Cp/PEG, ZIF-8/silica/GPt/PEG, Cp, and PEG. The treatment concentrations for all groups, except GPt and Cp, were 0.025 mg/mL, 0.05 mg/mL, 0.1 mg/mL, and 0.5 mg/mL. Further, cell treatment with Cp included the following observations. According to the drug loading experiment, there were 0.045 mg of Cp/1 mg of ZIF-8/silica/Cp and ZIF-8/Silica/Cp/PEG. Thus, the calculated actual concentrations of Cp in the experimental concentrations of the nanocomposites were 0.001125 mg/mL, 0.00225 mg/mL, 0.0045 mg/mL, and 0.0225 mg/mL. For example, 0.5 mg/mL of ZIF-8/silica/Cp or ZIF-8/silica/Cp/PEG will contain 0.0225 mg/mL of Cp.

Furthermore, cell treatment with GPt included the following observations. According to the drug loading experiment performed after leaf extraction, there was 0.1189 mg of GPt/1 mg of the leaf extract. The leaf extract stock solution was prepared at a concentration of 1.89 mg/mL, which means that the stock contains 0.225 mg/mL of GPt. Furthermore, the drug loading experiment performed after nanocomposite preparation showed that there were 0.045 mg of GPt/1 mg of ZIF-8/silica/GPt and ZIF-8/silica/GPt/PEG. Thus, the calculated actual concentrations of GPt in the experimental concentrations of the nanocomposites were 0.00945, 0.0189, 0.0378, and 0.189 mg/mL. For example, 0.5 mg/mL of ZIF-8/silica/GPt or ZIF-8/silica/GPt/PEG will contain 0.0225 mg/mL of GPt. Thus, if 1.89 mg/mL of the leaf extract stock solution contains 0.225 mg/mL of GPt, then 0.0225 mg/mL of GPt is equivalent to a concentration of 0.189 mg/mL of the GPt leaf extract solution.

Example 10: Cell Viability Assay

A MTT (3-(4,5-dimethylthiazol-2-yl)-2,5-diphenyltetrazolium bromide) assay was used to assess the cytotoxic capability of the GPt containing nanocomposite compared to the Cp containing nanocomposite. The principle of the assay depends on the ability of live cells to convert the yellow-colored MTT to the blue-colored formazan crystals. Briefly, MTT (Sigma-Aldrich) solution was added to cells at a concentration of 0.5 mg/mL and incubated at 37° C. for 4 h. After the incubation period, 0.04 N HCl isopropanol was added to dissolve the formazan crystals. After that, a plate reader SYNERGY-neo2, USA was used to measure the absorbance at 570 nm. Two readings were taken before and after the addition of MTT. The first reading was subtracted from the second reading to eliminate unspecific interference. The analysis was performed in comparison with the untreated control. The percentage viability was calculated as treated/control×100. These results were then used to calculate the half-maximal effective concentration ($EC_{50}$) using GraphPad Prism 10.0.3 software.

Example 11: Statistics

The cytotoxicity assay was repeated in three biological replicates. GraphPad Prism 10.0.3 software was used for statistical analysis. The analysis was performed using two-way ANOVA with Dunnett's multiple-comparison post hoc test. SEM diagrams represent error bars±standard error of the mean.

Example 12: Composite Characterization

Figure 1B:
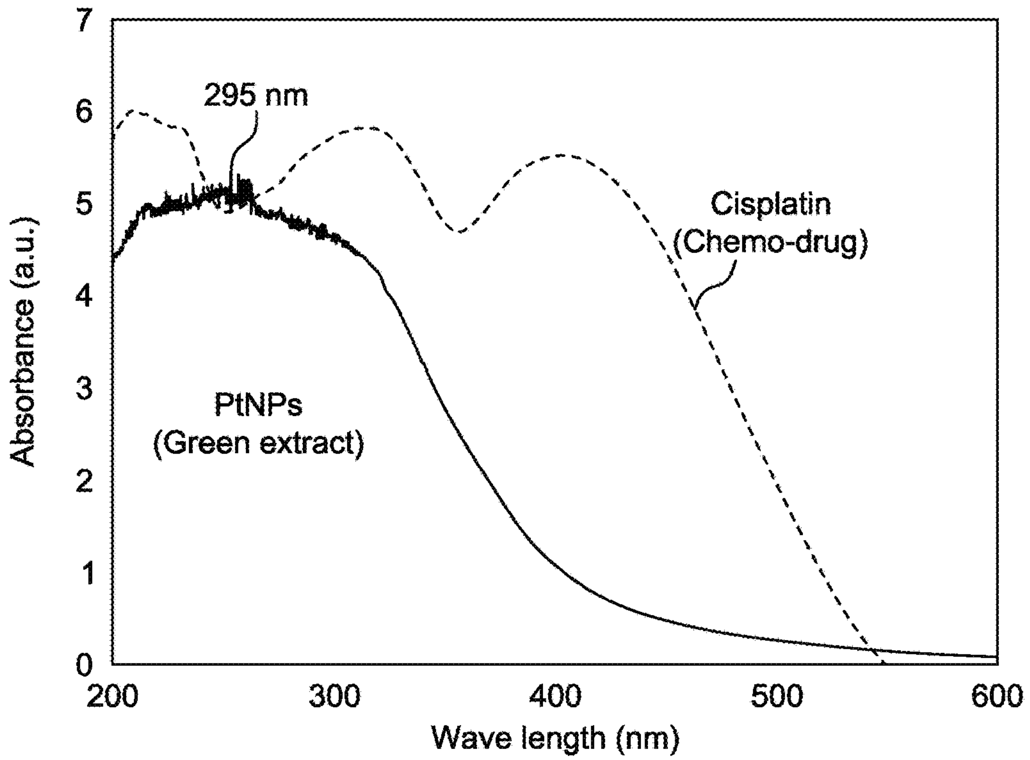
FIG. 1B shows ultraviolet (UV)-visible absorption spectra of the Pt NPs and cisplatin (CPt), according to certain embodiments.

Green platinum nanoparticles (PtNPs) are synthesized using neem leaf extract. The PtNPs were analyzed using ultraviolet (UV) visible spectroscopy, as shown in FIG. 1B. In accordance with the present disclosure, the bio-reduction of cisplatin to biogenic $Pt^0$ NPs mediated by neem leaves was confirmed with two characteristic changes, including the occurrence of a broad peak between 200 nanometers (nm) and 400 nm, and color change. $Pt^{4+}$ and $Cl^-$ ions of plant extract exhibit a sharp absorption peak at about 260 nm due to the process of ligand-to-metal transition. During the reduction process from $Pt^{4+}$ to $Pt^0$, a sharp decrease in the absorption peak at 260 nm occurs, and conversely, a wide absorption peak confirms the complete reduction to $Pt^0$ species. In some aspects of the present disclosure, the presence of such a broad surface plasmon resonance peak with peak maxima at about 295 nm confirms the effective reduction of cis-$[Pt(NH_3)_2Cl_2]$ and formation of Pt NPs. In addition, the qualitative confirmation of PtNPs was also obtained with the sample color changing from yellow to black.

Figure 1C:
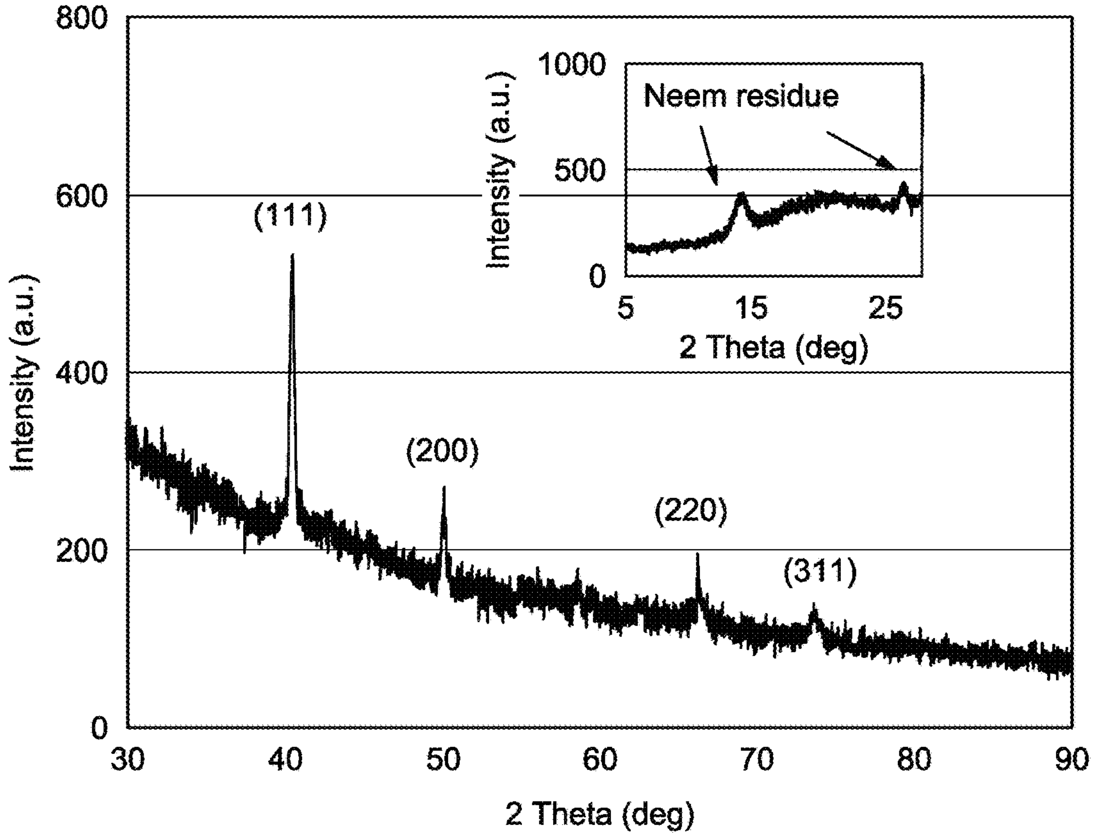
FIG. 1C depicts an X-ray diffraction (XRD) pattern of the Pt NPs, according to certain embodiments.

FIG. 1C shows X-ray diffraction (XRD) pattern of PtNPs. The presence of platinum nanoparticles with face-centered cubic crystals was confirmed at 40.5°, 50°, 66°, and 74°, corresponding to the presence of (111), (200), (220), and (311) planes (JCPDS Card 04-0802). A slight shift in the (111) plane from 39.8° towards the higher angle of 40.5° is attributed to Pt alloy formation. Further, an effective reduction of cisplatin by neem leaves was also revealed along with the formation of the face-centered cubic crystalline phase of PtNPs.

Figure 2A:
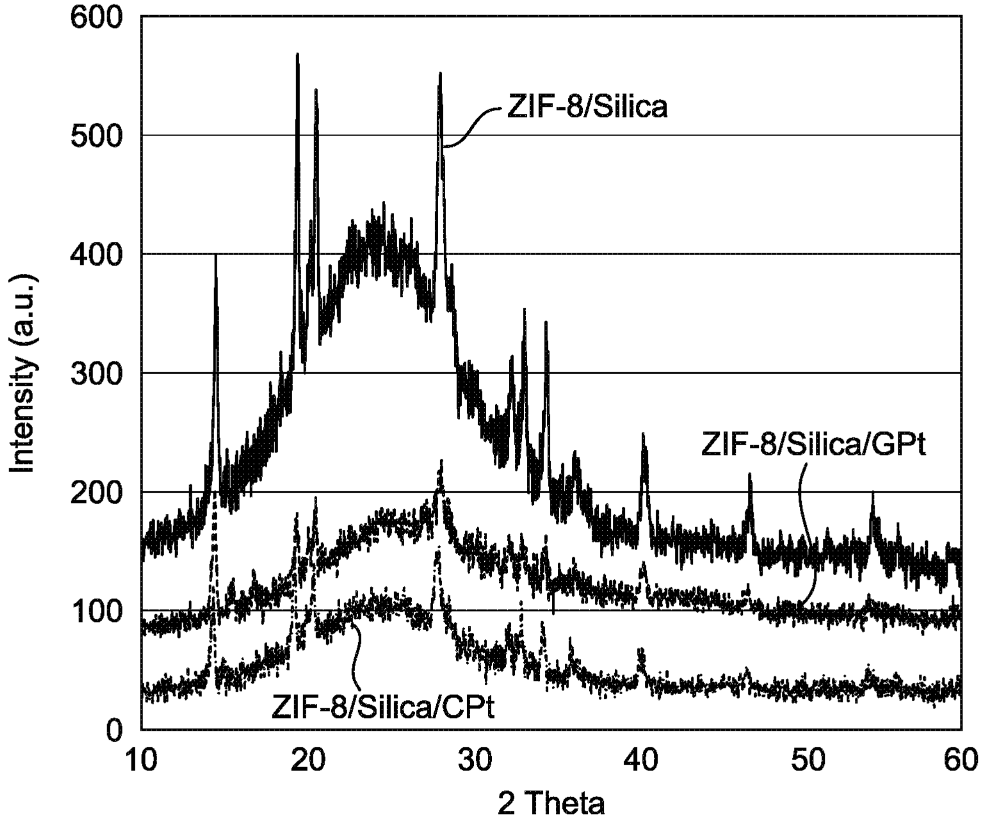
FIG. 2A depicts XRD patterns of zeolitic imidazolate framework (ZIF-8)/silica, ZIF-8/silica/CPt, and ZIF-8/silica/GPt, according to certain embodiments.
Figure 2B:
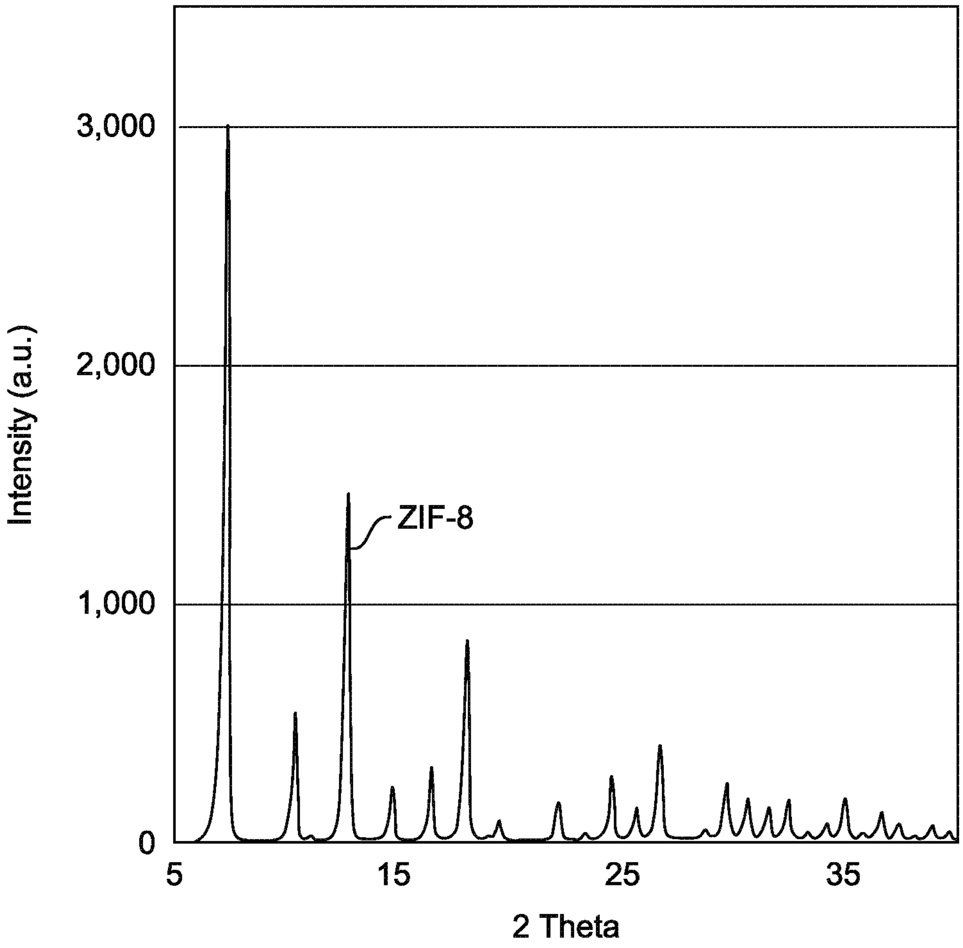
FIG. 2B depicts an XRD pattern of ZIF-8, according to certain embodiments.
Figure 2C:
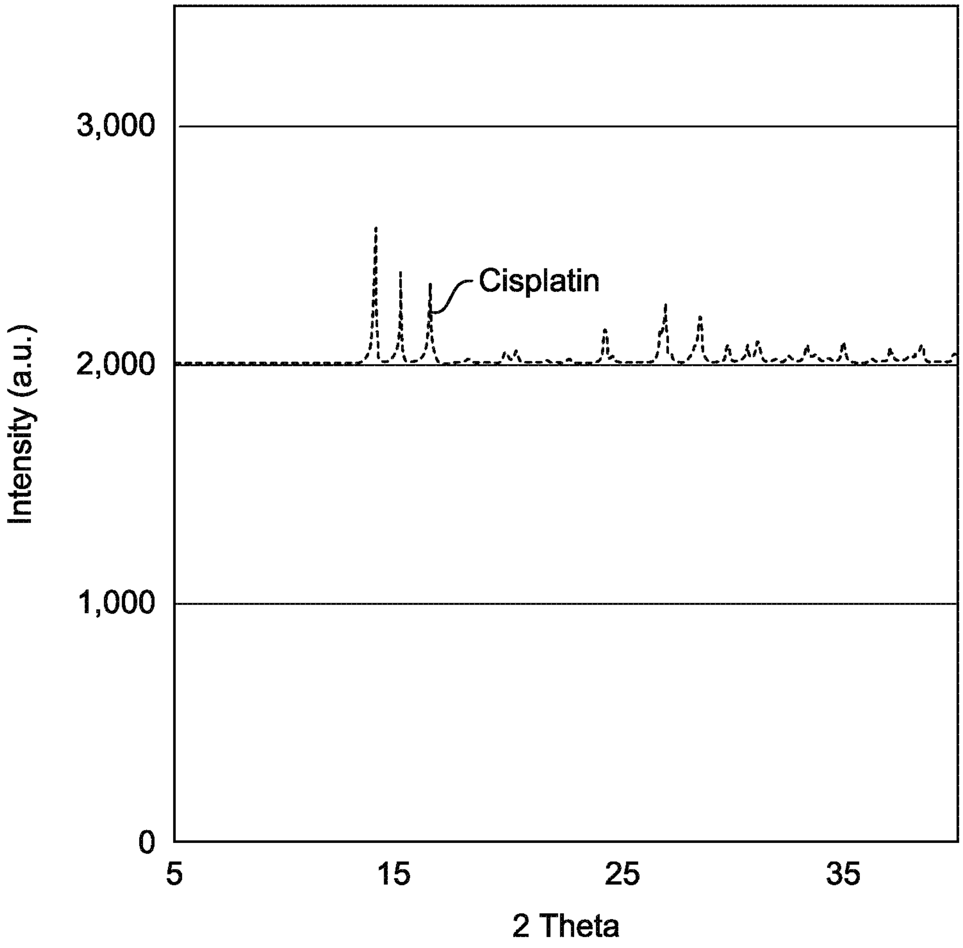
FIG. 2C depicts an XRD pattern of cisplatin, according to certain embodiments.

The phase of ZIF-8 and transformation with silica nanocomposite formation was analyzed by XRD analysis, as shown in FIG. 2A. In the case of parent ZIF-8, crystalline peaks were observed at the 2-theta range 5° to 60° corresponding to the structure of rhombic dodecahedral (sodalite), as shown in FIG. 2B. Similarly, cisplatin showed well-resolved crystalline peaks corresponding to the Pt complex, as shown in FIG. 2C. In the case of ZIF-8/silica nanocomposites (ZIF-8/silica, ZIF-8/silica/GPt, and ZIF-8/silica/CPt), a broad amorphous peak corresponding to the silica appears with peak maxima at 2 theta range of 22°, as shown in FIG. 2A. In addition, residual peaks of ZIF-8 with reduced intensity appear, indicating the integration of nanocarrier zeolitic imidazolate framework (ZIF-8) into silica forming a unique ZIF-8/silica nanocomposite formation.

Figure 2D:
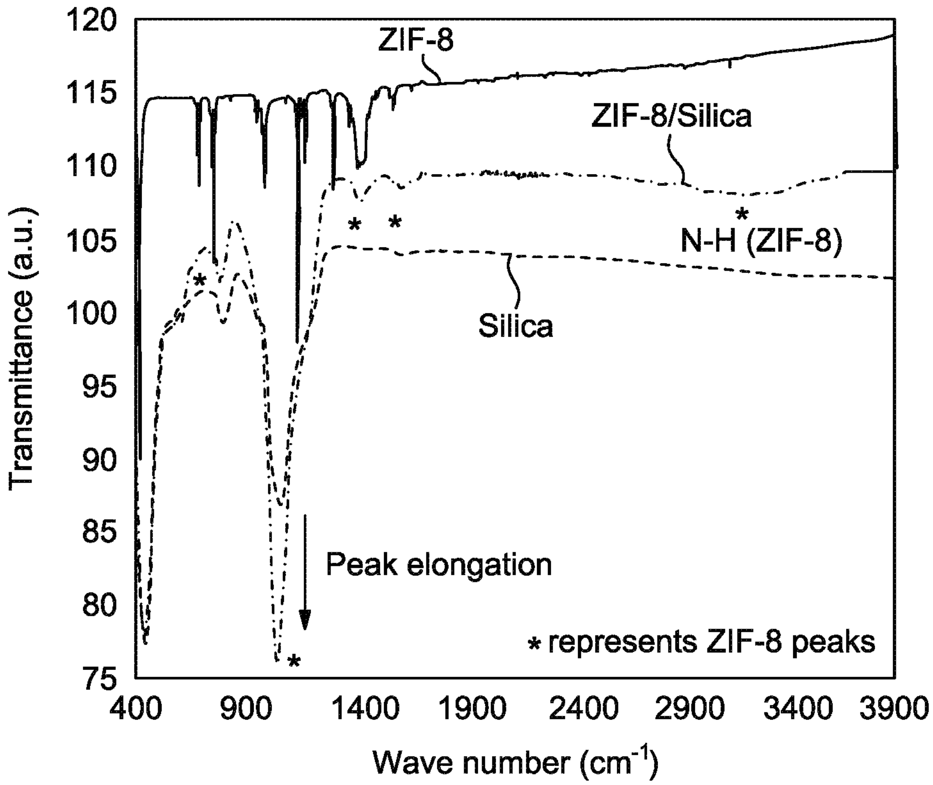
FIG. 2D depicts Fourier transform infrared spectroscopy (FTIR) spectra of ZIF-8, silica, and ZIF-8/silica, according to certain embodiments.

ZIF-8/silica transformation occurs due to the decoration process of silica. The functional groups of ZIF-8, ZIF-8/silica nanocomposite, and silica were analyzed using Fourier transform infrared spectroscopy (FTIR) spectroscopy, as shown in FIG. 2D. ZIF-8 showed stretching vibration bands of imidazole corresponding to —C═N— at 1584 $cm^{-1}$ along with stretching peaks of the five-membered ring between 1311 and 1512 $cm^{-1}$. The stretching and bending of the —C—N bond was observed at 1147 $cm^{-1}$ and 966 $cm^{-1}$, respectively. Further, the —C—H bending of the double bond was observed at 761 cm 1, along with ring out-of-plane bending vibration at 695 $cm^{-1}$. The linkage between the $Zn^{2+}$ ion and imidazole ring were confirmed with —Zn—N stretching at 426 $cm^{-1}$. In the case of ZIF-8/silica nanocomposite formation, the functional moieties of ZIF-8 confirm the intactness of the sodalite structure, while silica functional peaks indicate the intrusion of silica at the core surface of the ZIF-8.'

Figure 2E:
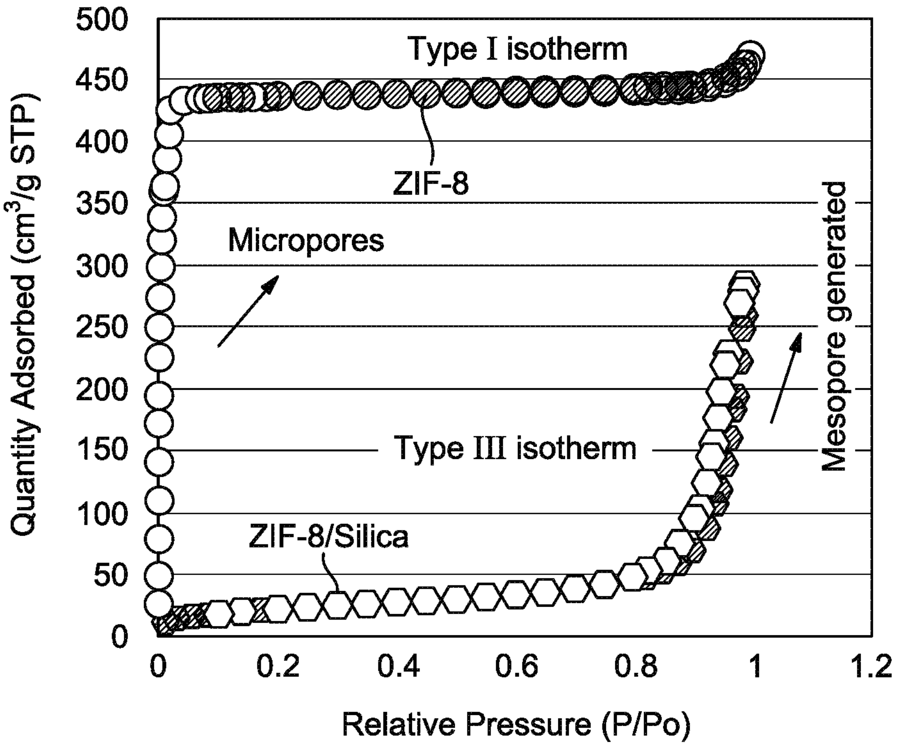
FIG. 2E depicts nitrogen adsorption-desorption isotherm of ZIF-8 and ZIF-8/silica, according to certain embodiments.
Figure 2F:
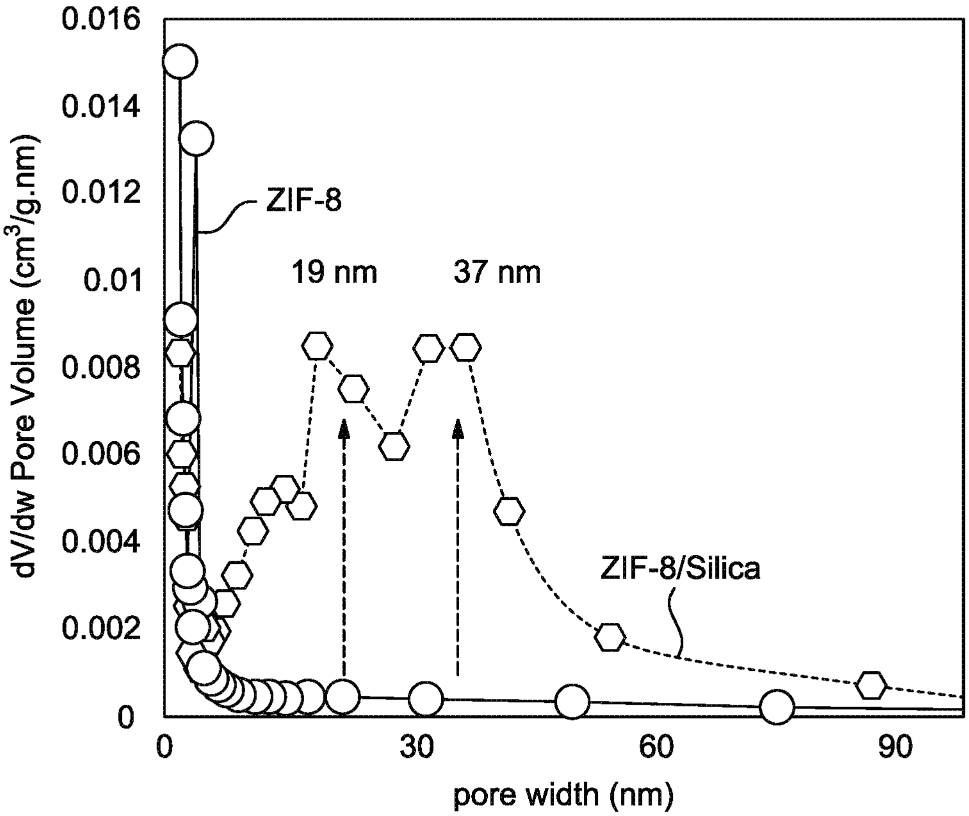
FIG. 2F depicts pore size distributions of ZIF-8 and ZIF-8/silica nanocomposite, according to certain embodiments.

The textural properties of ZIF-8 and ZIF-8/silica nanocomposite were analyzed using a nitrogen adsorption isotherm technique, as shown in FIG. 2E and FIG. 2F. ZIF-8 showed micropore filling characteristics at a $P/P^0$ value less than 0.2, with a surface area of about 1217 $m^2/g$. as shown in FIG. 2E and Table 1. The t-plot analysis showed a major portion of the micropore surface area of about 1181 $m^2/g$, while the mesoporous surface contributed to about 36 $m^2/g$. The pore volume of ZIF-8 was about 0.72 $cm^3/g$, with an average pore size distribution of 2.35 nm. In the case of ZIF-8/silica nanocomposite, the mesoporous silica hybrid formation with ZIF-8 was confirmed with the generation of a hysteresis loop. Furthermore, the micropore surface area reduced proportionately, thereby producing mesopores exhibiting a type III hysteresis loop at a higher P/P° value of 0.9, with a surface area of 75 $m^2$/g. as shown in FIG. 2E. The pore size distribution showed the presence of dual types of mesopores centered at 19 nm and 37 nm, respectively. This shows a unique hybrid nanocomposite formation of silica with ZIF-8, as shown in FIG. 2F.

TABLE 1

Textural properties of ZIF-8 and ZIF-8/silica nanocomposite

| Sample | BET surface area ($m^2$/g) | t-Plot micro SA ($m^2$/g) | Meso SA ($m^2$/g) | Pore Volume ($cm^3$/g) | Pore Size (nm) |
|---|---|---|---|---|---|
| ZIF-8 | 1217 | 1182 | 35 | 0.72 | 2.3 |
| ZIF-8/silica | 75 | — | 75 | 0.44 | 23.5 |

Figure 3:
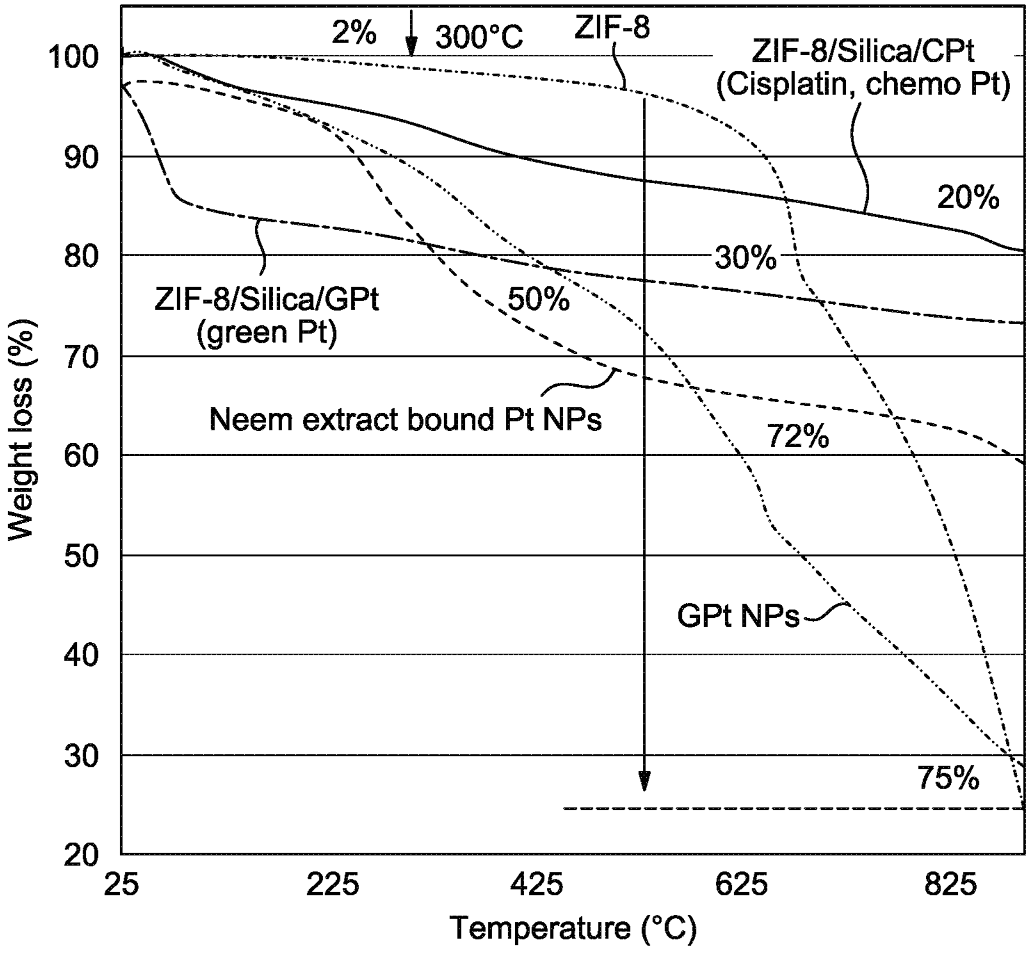
FIG. 3 depicts thermogravimetric analysis (TGA) of ZIF-8, ZIF-8/silica, green platinum (GPt) NPs, ZIF-8/silica/GPt, and ZIF-8/silica/CPt, according to certain embodiments.

TGA was used to measure the thermal stability and decomposition trend of ZIF-8 and ZIF-8-based nanocomposites. The thermal stability and decomposition pathway trend of ZIF-8, ZIF-8/Silica, green platinum nanoparticles (GPt NPs), ZIF-8/silica/GPt, and ZIF-8/silica/CPt were measured using TGA under argon atmosphere, as shown in FIG. 3. In the case of ZIF-8, an initial weight loss of around 2%, attributed to the solvent evaporation and imidazole linker that is physically adsorbed on the external and internal framework of ZIF-8, was observed up to 300° C. As the temperature increased past 300° C., a distinct weight loss occurred, corresponding to the structural disintegration of ZIF-8 crystals. The decomposition curve subsequently increases steeply, with a total mass loss of about 75% at temperatures greater than 300° C., thereby confirming the carbonization under heat treatment leading to the formation of ZnO. Further, the interaction of ZIF-8 with silica through one-pot synthesis was found to improve the thermal stability of nanocomposite ZIF-8/Silica. From the initial temperature to 400° C., a weight loss of about 19% was observed, indicating the removal of adsorbents from the ZIF-8. Upon further increasing the temperature, a gradual weight loss of about 72% was observed in the ZIF-8/silica profile, as shown in FIG. 3, which was lower compared to that of ZIF-8 (75%). A variable pattern of weight reduction in the nanocomposite compared to ZIF-8 indicates improved stability of ZIF-8 nanocrystals with a coating of silica. Furthermore, FIG. 3 shows the mass loss of GPt obtained from neem leaf extract. The incurred weight loss between 100° C. and 310° C. of about 20% was ascribed to cellulosic components, while the decomposition of phytochemicals from neem leaf extract occurs between 300° C. and 600° C. The degradation is complete at 600° C. to 900° C., with a total weight loss of about 50%. TGA analysis of GPt-loaded nano formulation ZIF-8/Silica/GPt incurred a mass loss of 30%, thereby confirming the presence of phytochemicals similar to that of GPt. The profile of ZIF-8/Silica/CPt including cisplatin revealed a lower level of disintegration, with mass loss of 20% between 25° C. and 900° C.

Figure 4:
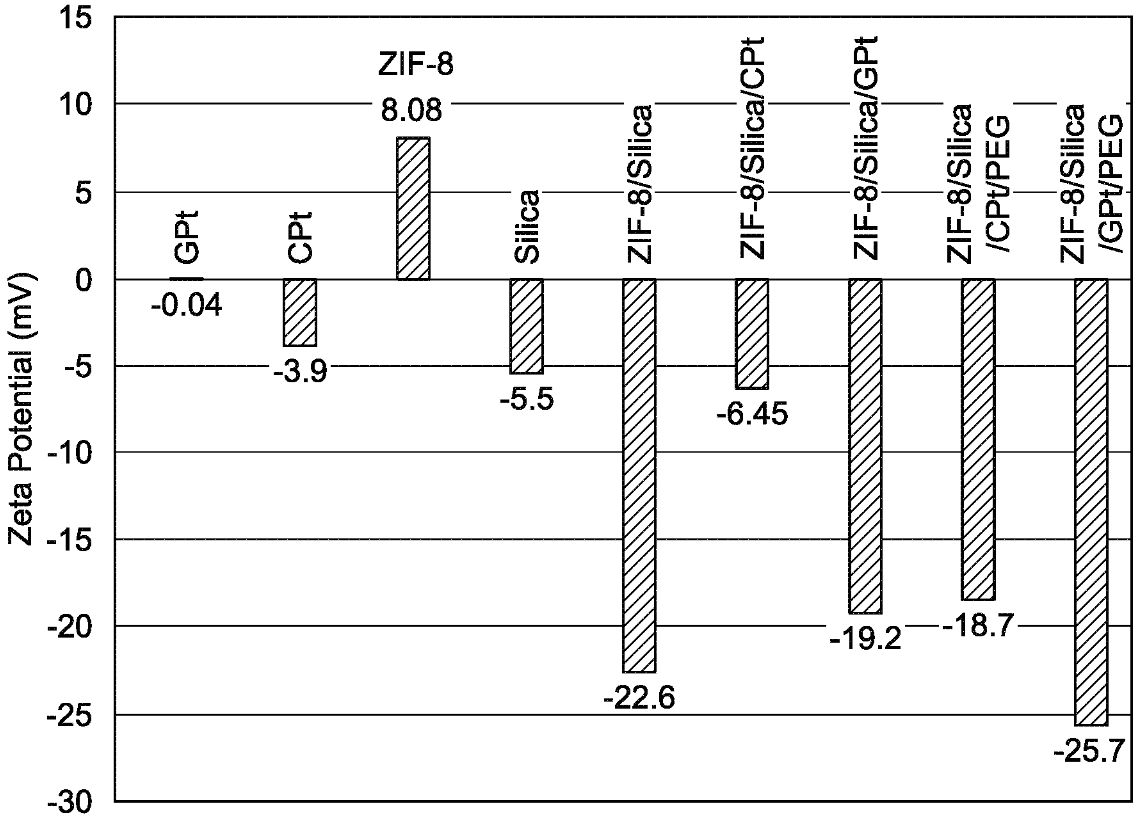
FIG. 4 depicts zeta potential of GPt NPs, CPt, ZIF-8, silica, ZIF-8/silica, ZIF-8/silica/CPt, ZIF-8/silica/GPt, ZIF-8/silica/CPt/PEG, and ZIF-8/silica/GPt/PEG nanocomposites, according to certain embodiments.

The zeta potential measurement of synthesized nanomaterials indicates the charge and colloidal state stability of nanoparticles. FIG. 4 shows the zeta potential of green PtNPs (GPt), cisplatin (CPt), ZIF-8, silica, ZIF-8/silica, ZIF-8/silica/CPt, ZIF-8/silica/GPt, ZIF-8/silica/CPt/PEG, and ZIF-8/Silica/GPt/PEG nanocomposites. As such, the precursor ZIF-8 showed a positive zeta potential of +8.08 mV, while silica showed a negative zeta potential of −5.5 mV. Cisplatin and green-synthesized platinum nanoparticles showed less negative zeta potentials of −3.9 mV and −0.04 mV, respectively. The combination of ZIF-8/silica showed a large negative value of −22.6 mV, indicating effective composite formation. In general, the potential measurements of the samples ranged from −22.6 mV to −25.7 mV, demonstrating dispersion stability caused by repelling interactions between nanoparticles. In case of CPt functionalization, the zeta potential of ZIF-8/Silica/CPt decreases to −6.45 mV, while ZIF-8/Silica/GPt shows stabilization with green PtNPs, with a value of −19.2 mV, composed of flavonoids and polyphenols. The size distribution measured using dynamic light scattering (DLS) of ZIF-8/silica shows an average size diameter of 754 nm. After the loading of PtNPs and pegylation, the average particle size decreases to 125 nm. The higher hydrodynamic size distribution observed using the DLS technique compared to TEM shows the effect of hydration.

Figure 5A:
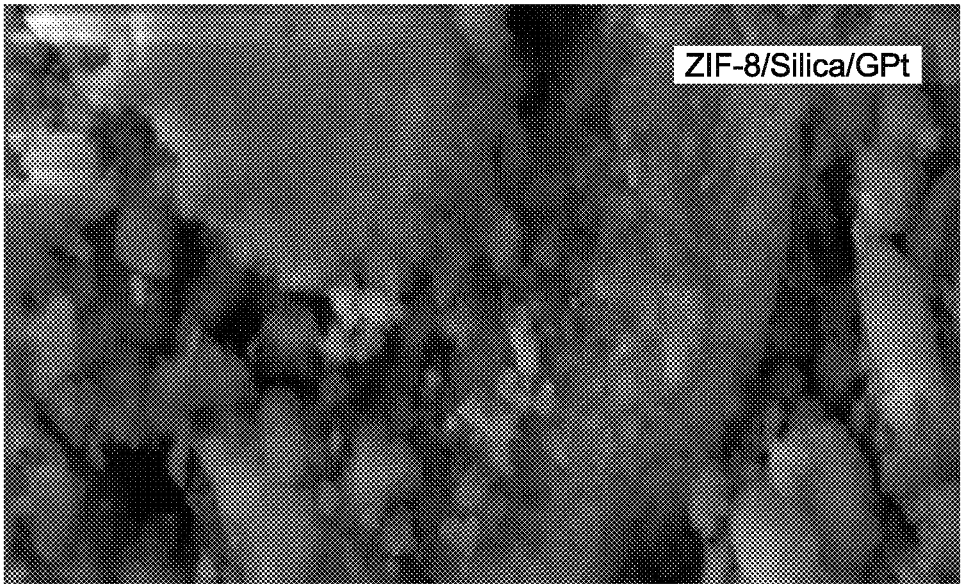
FIG. 5A is an optical image of scanning electron microscopy (SEM) of ZIF-8/silica/GPt, according to certain embodiments.
Figure 5B:
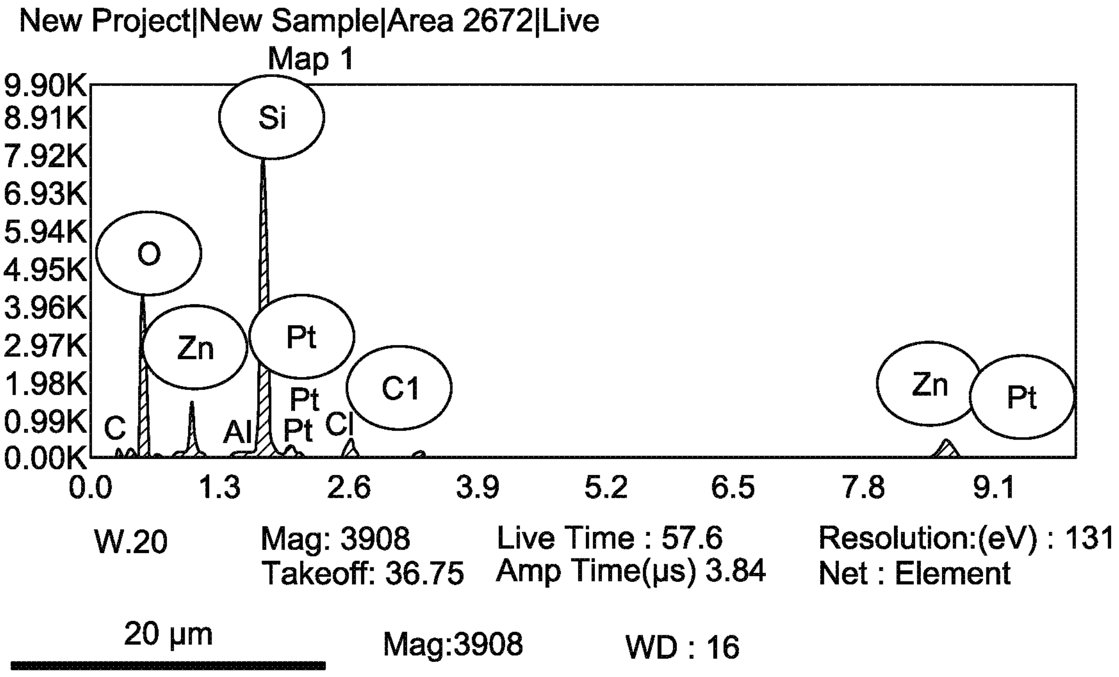
FIG. 5B shows energy dispersive X-ray spectroscopy (EDX) results for ZIF-8/silica/GPt, according to certain embodiments.
Figure 5C:
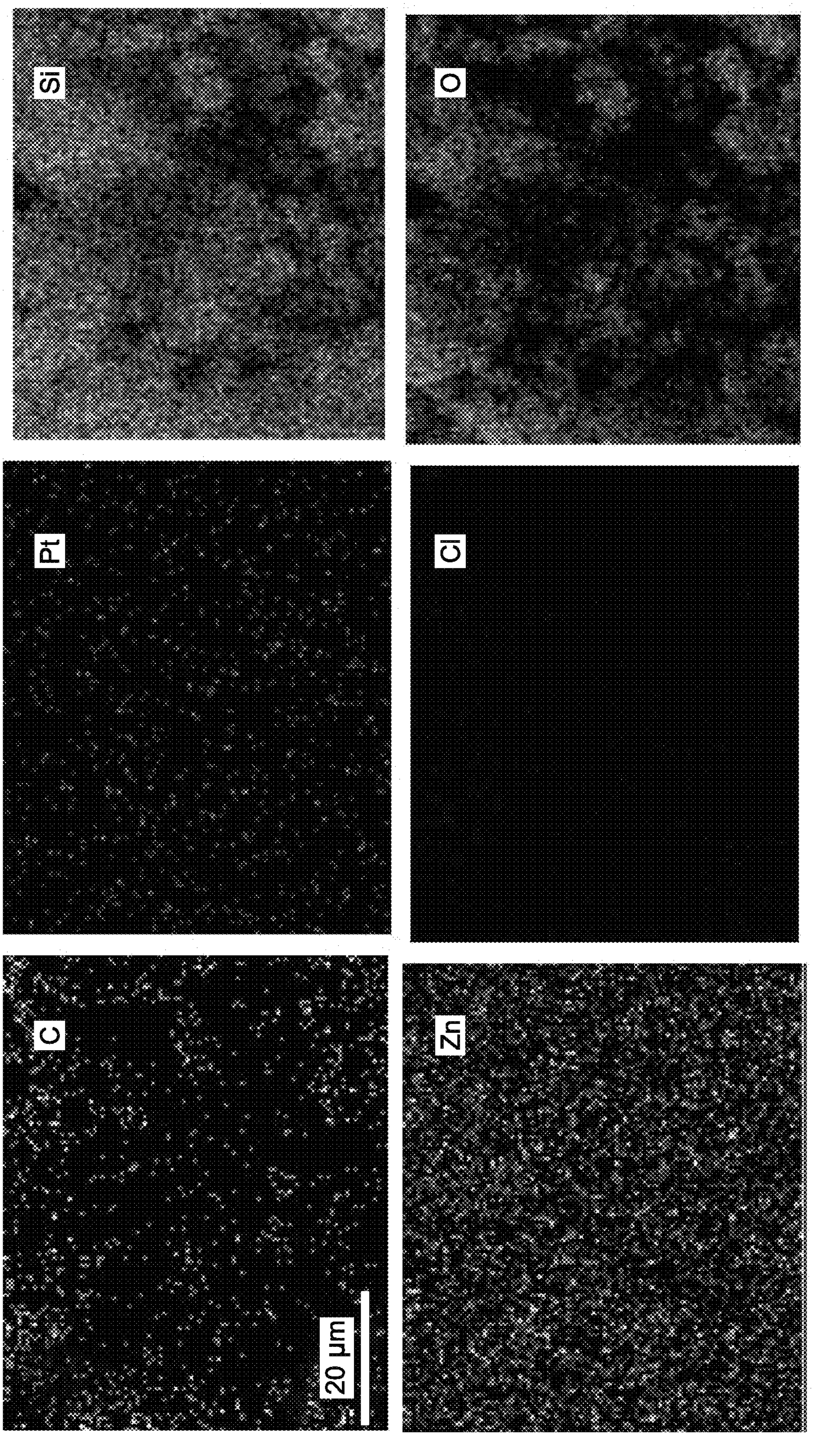
FIG. 5C shows SEM-EDX images of ZIF-8/silica/GPt, at 20 micrometers (μm) magnification for C, Pt, Si, Zn, Cl and O, according to certain embodiments.
Figure 5D:
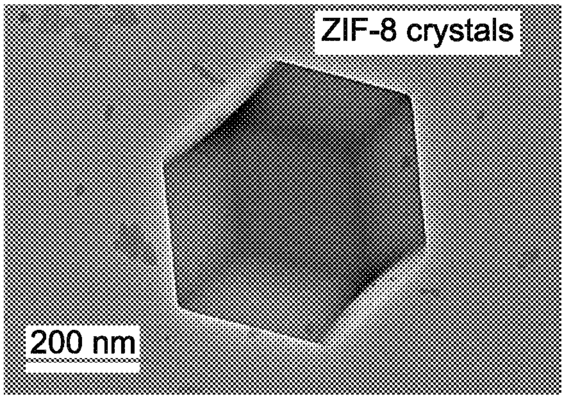
FIG. 5D is a high-resolution transmission electron microscopy (HRTEM) image of ZIF-8, according to certain embodiments.
Figure 5E:
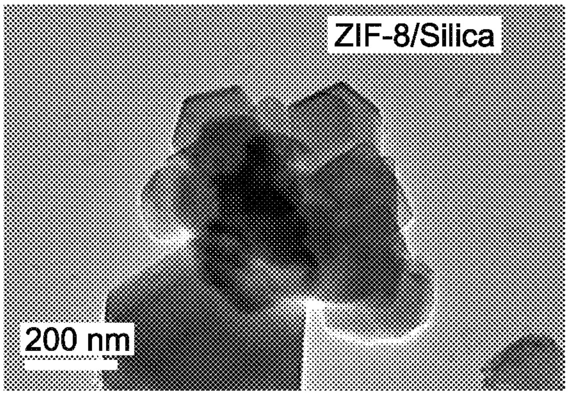
FIG. 5E is a HRTEM image of ZIF-8/silica at a magnification of 200 nanometres (nm), according to certain embodiments.
Figure 5F:
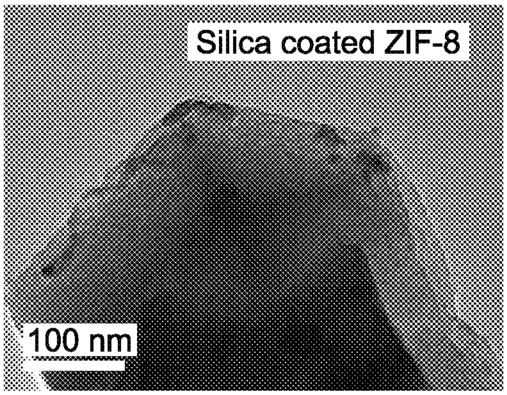
FIG. 5F is a HRTEM image of ZIF-8/silica at a magnification of 100 nm, according to certain embodiments.
Figure 5G:
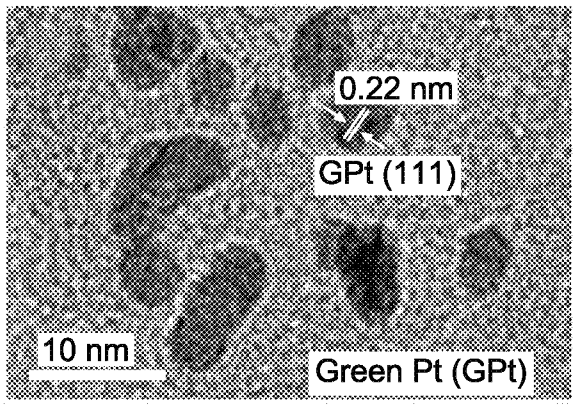
FIG. 5G is a HRTEM image of GPt, according to certain embodiments.
Figure 5H:
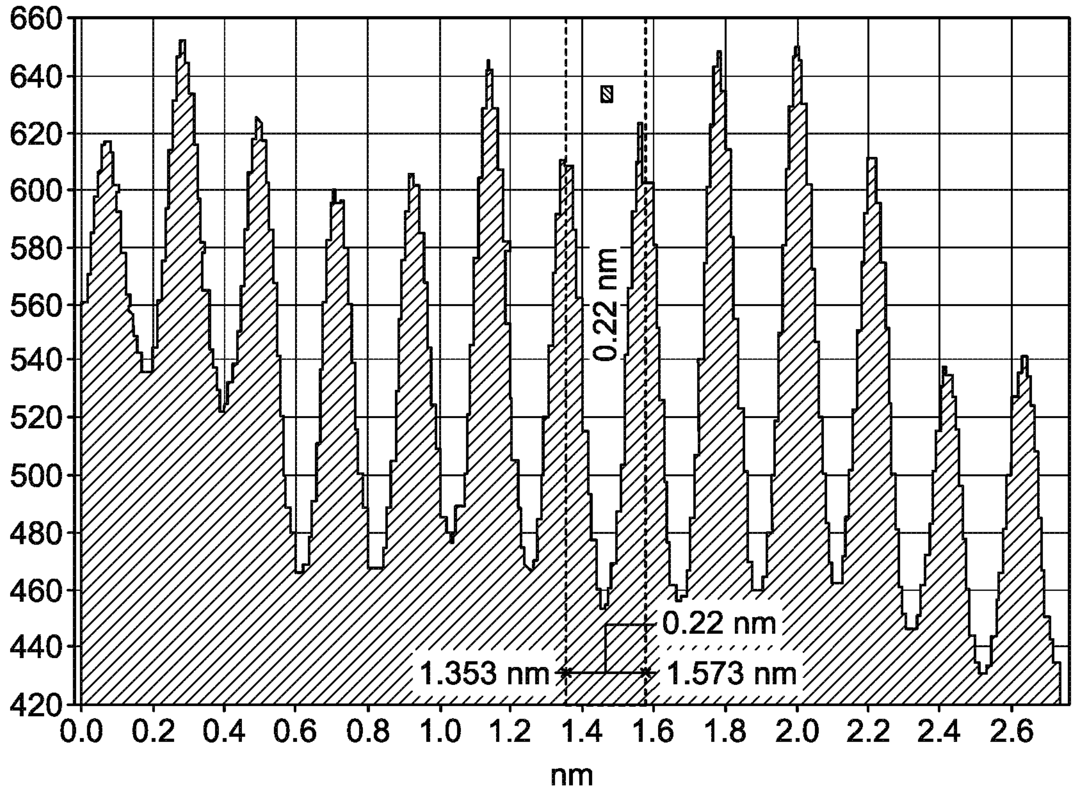
FIG. 5H is an optical image of d-spacing measured from lattice fringes of GPt, according to certain embodiments.
Figure 5I:
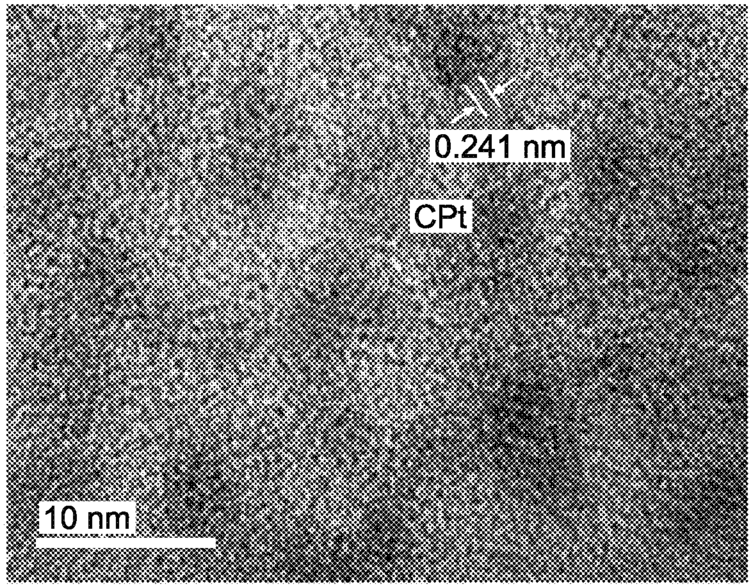
FIG. 5I is an optical image of d-spacing measured from lattice fringes of ZIF-8/silica, according to certain embodiments.
Figure 5J:
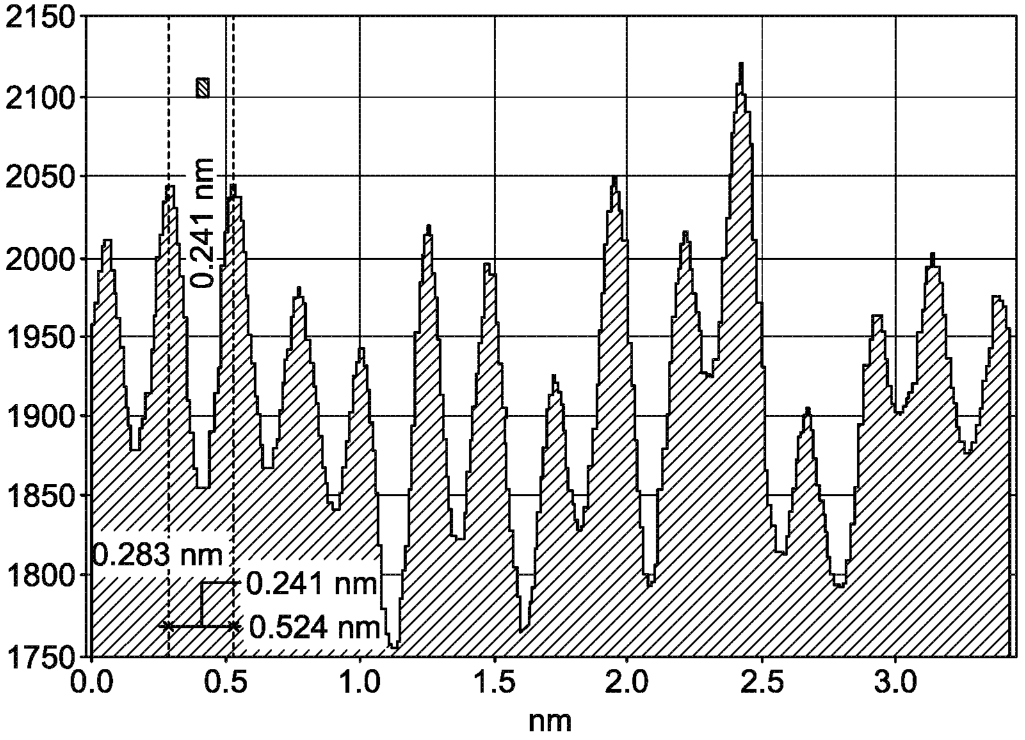
FIG. 5J is an optical image showing d-spacing of ZIF-8/silica/CPt, according to certain embodiments.
Figure 5K:
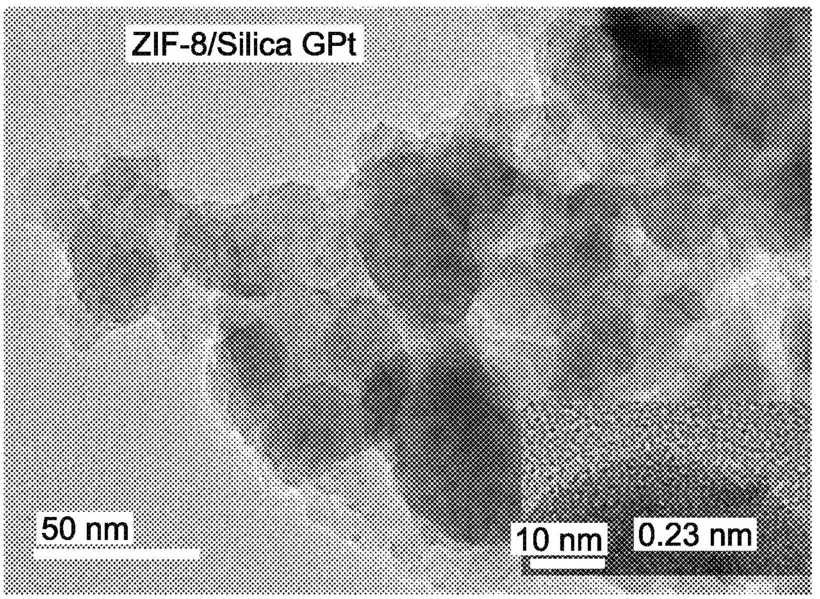
FIG. 5K is an optical image showing d-spacing of ZIF-8/silica/GPt, according to certain embodiments.
Figure 5L:
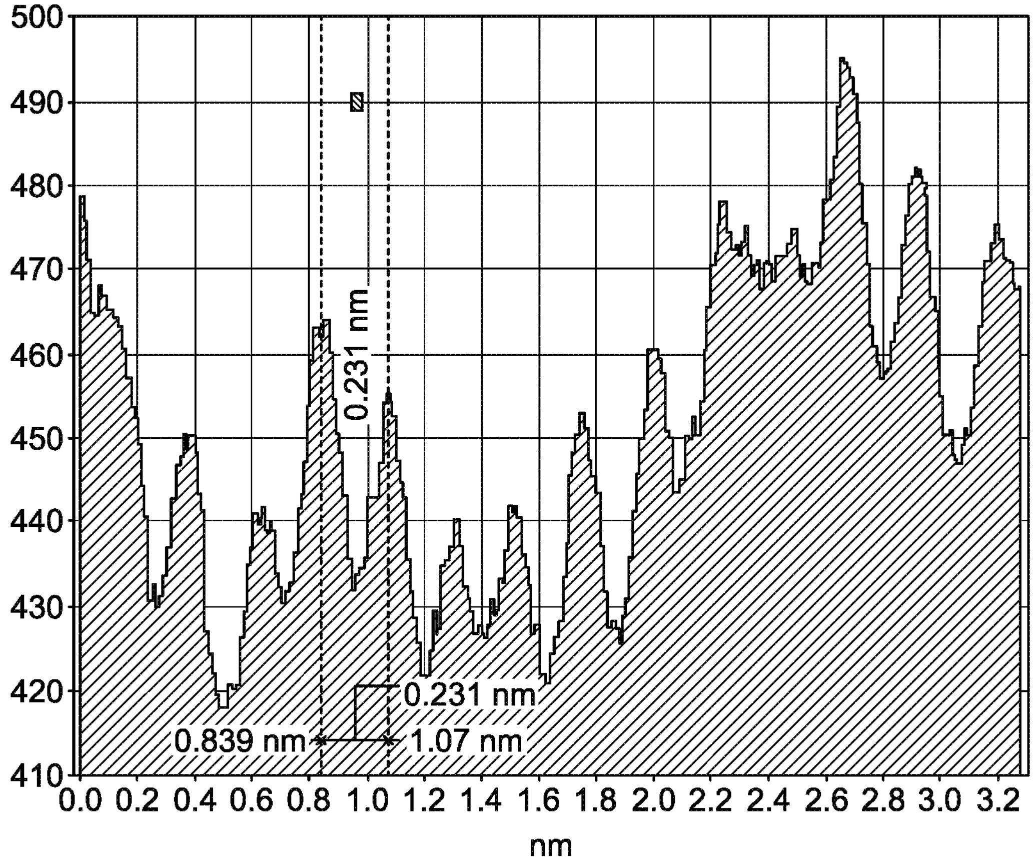
FIG. 5L is an optical image showing d-spacing of ZIF-8/silica/GPt, according to certain embodiments.

FIGS. 5A-5C show the scanning electron microscopy (SEM) and energy dispersive X-ray (EDX) images of ZIF-8/silica/GPt. FIG. 5D shows high resolution transmission electron microscopy (HRTEM) images of ZIF-8. FIGS. 5E-5F shows HRTEM of ZIF-8/silica. FIG. 5G shows HRTEM green Pt. FIG. 5H shows HRTEM d-spacing measured from lattice fringes of GPt. FIG. 5I shows HRTEM of ZIF-8/Silica/CPt. FIG. 5J shows HRTEM d-spacing of ZIF-8/Silica/CPt. FIG. 5K shows HRTEM of ZIF-8/Silica/GPt, and FIG. 5L shows HRTEM of ZIF-8/Silica/CPt. The utilization of SEM-EDX enables a rapid and nondestructive assessment of the elemental composition of a given sample, facilitating the prompt identification of its constituent components.

The SEM images of ZIF-8/silica/GPt are shown in FIG. 5A. After treatment of ZIF-8 in the Stober synthesis, the formation of ZIF-8/silica nanocomposite showed a variation in the morphology as agglomerated nanoparticles that are different than the crystal form of ZIF-8. Elemental mapping analysis confirmed the distribution of compositions in ZIF-8/silica/GPt nanocomposite. In case of ZIF-8/Silica/GPt, the analysis revealed the abundant presence of carbon, nitrogen, and oxygen, corresponding to the components of neem extract and imidazole of ZIF-8. The crystal mapping reveals a homogeneous dispersion of silica within the ZIF-8/silica framework, as shown in FIGS. 5A-5C. The presence of platinum and chlorine is confirmed on the surface of ZIF-8/Silica/GPt. However, detailed examinations of other characterization techniques, such as UV-visible, XRD (FIG. 1B), and TGA (FIG. 3), showed the different forms of Pt nanoparticles based on the two sources, such as cisplatin alone and neem leaves.

FIG. 5D shows that the morphology of raw ZIF-8 exhibits uniform-sized, bigger particle crystallites with rhombic dodecahedral shape in the range of about 500 nm. As can be seen from FIGS. 5E-5F, in case of ZIF-8/silica nanocomposite, an interrelated structure consisting of dark-shaped ZIF-8 was observed along with a lighter phase of silica. On comparative scale bar analysis of 200 nm, a significant reduction is confirmed concerning the crystal sizes of about 250 nm to 500 nm of ZIF-8. Furthermore, the Zn of ZIF-8 in silica was evident with the lattice fringes of $Zn^{2+}$ (0.2515 nm) surrounded by the silica layers. This result was consistent with the results of the XRD diffraction pattern, as discussed above with reference to FIG. 2A, FTIR functional groups of ZIF-8 in ZIF-8/silica as discussed above with reference to FIG. 2D, and elemental composition of SEM-EDX as discussed above with reference to FIG. 5A. Referring to FIG. 5H, FIG. 5J, FIG. 5I, respectively, the d-spacing arrangement in green PtNPs, ZIF-8/Silica/CPt, and ZIF-8/silica/GPt nanocomposites was determined by using lattice fringes. As can be seen from FIG. 5G, GPt NPs synthesized using neem leaf extract showed the presence of agglomeration associated with large chunks, typical of the leaf extract-bound nanoparticles. Green route synthesized PtNPs using neem leaf extract showed variable particles in the range of 4 nm to 10 nm. The presence of metallic Pt (111) in green synthesis was confirmed with the interplanar spacing value of 0.22 nm, as shown in FIG. 5H. Moreover, FIG. 5I shows the dispersion of cisplatin-derived Pt in the range of 4 nm to 10 nm on the ZIF-8/silica support. In case of ZIF-8/Silica/CPt, the morphological structure of ZIF-8/silica after functionalization with cisplatin remains similar to that of parent ZIF-8/silica nanocomposite. The functionalization of GPt on ZIF-8/silica showed irregularly shaped particles in the form of clusters attributed to the leaf extract. In case of GPt loading on ZIF-8/silica, a highly monodispersed PtNPs occurs with a particle size of about 5 nm, with interplanar spacing values of 0.2 and 0.23 nm, as depicted in FIGS. 5K-5L.

Example 13: Composite Performance

Figure 6:
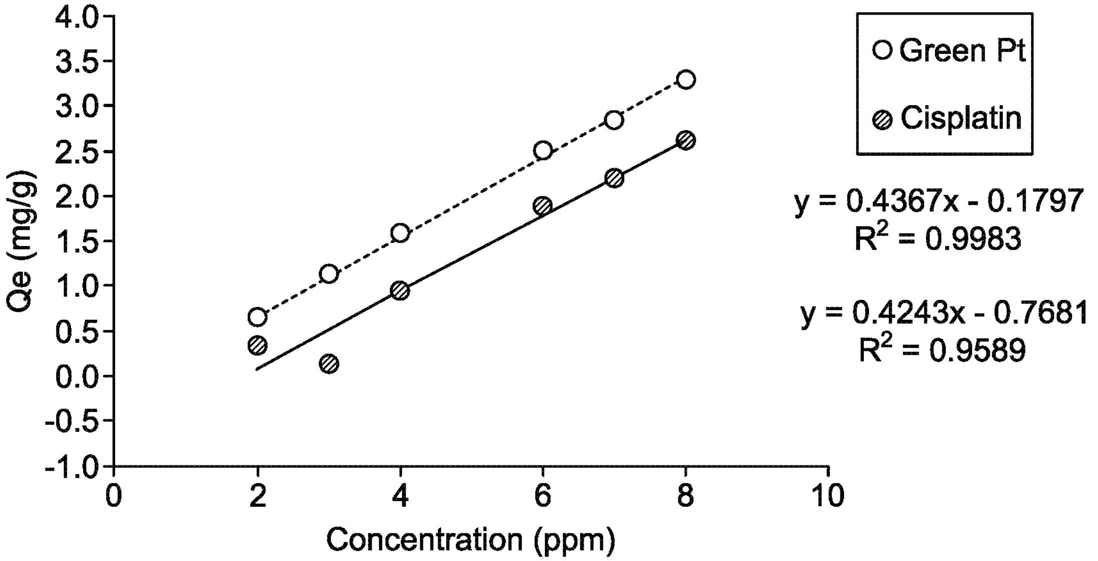
FIG. 6 depicts sorption of GPt and CPt by a nanocarrier at different initial concentrations, according to certain embodiments.

The initial concentration of Pt metal ions reflects the rate of sorption, which therefore is a factor to acquire the effectiveness of biosorption. To determine the highest concentration, metal solution concentrations ranging from 2 parts per million (ppm) to 8 ppm were investigated experimentally for the Pt metal. The removal efficiency (%) was highest at the maximum concentrations, and vice versa, whereas the percentage removal (%) was lowest at the minimum concentration for both green Pt and cisplatin, where the metal ions were removed as follows for the increased concentration. The removal efficiency (%) of green Pt had a higher magnitude value than cisplatin. Further, as illustrated in FIG. 6 and Table 2, the initial solution concentration has a direct relationship with the adsorptive capacity of green Pt and cisplatin onto the nanocarrier. This is illustrated by the fact that when there is an increase in the concentration of the particles, the metal ions rapidly fill the available sites until they are all occupied. This behavior of ion uptake onto the nanocarrier sample can be explained as a result of more favorable sites for ions to be adsorbed when the metal concentration is increased. In conclusion, it may be estimated that green Pt compounds are more selective for nanocarrier than cisplatin.

TABLE 2

Sorption of GPt and cisplatin by nanocarrier at different initial concentrations

| $C_0$ (ppm) | GPt Qe (mg/g) | Removal efficiency(%) | Cisplatin Qe (mg/g) | Removal efficiency (%) |
|---|---|---|---|---|
| 3 | 1.14 | 75.9 | 0.14 | 9 |
| 4 | 1.59 | 79.5 | 0.95 | 47.5 |
| 6 | 2.51 | 83.67 | 1.89 | 62.83 |
| 7 | 2.84 | 81.14 | 2.2 | 62.71 |
| 8 | 3.29 | 82.25 | 2.62 | 65.38 |

Figure 7A:
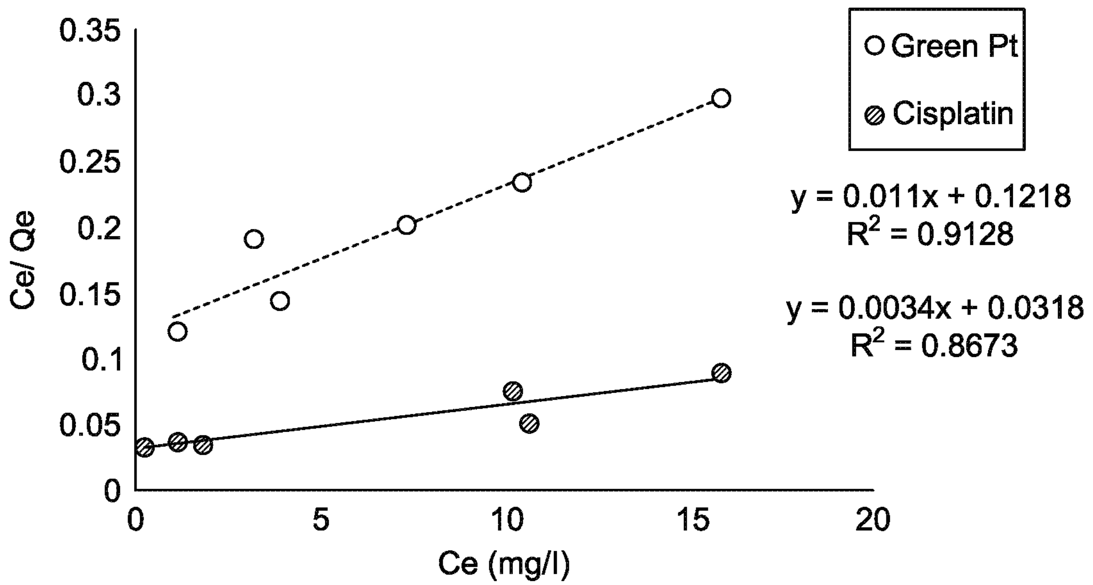
FIG. 7A depicts Langmuir isotherm sorption of GPt and CPt by nanocarriers, according to certain embodiments.
Figure 7B:
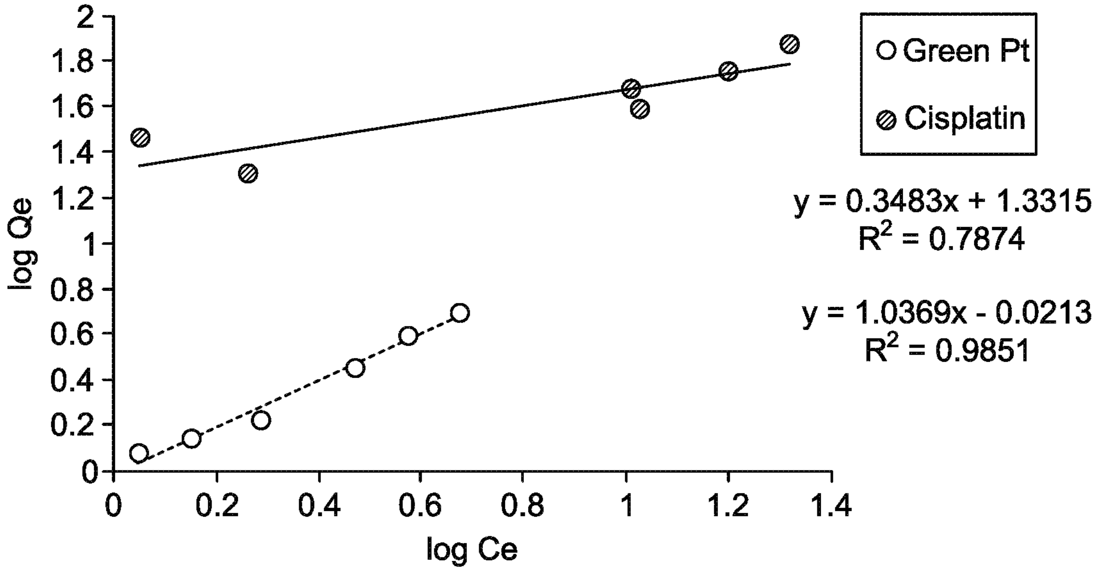
FIG. 7B depicts Freundlich isotherm sorption of GPt and CPt by nanocarriers, according to certain embodiments.
Figure 7C:
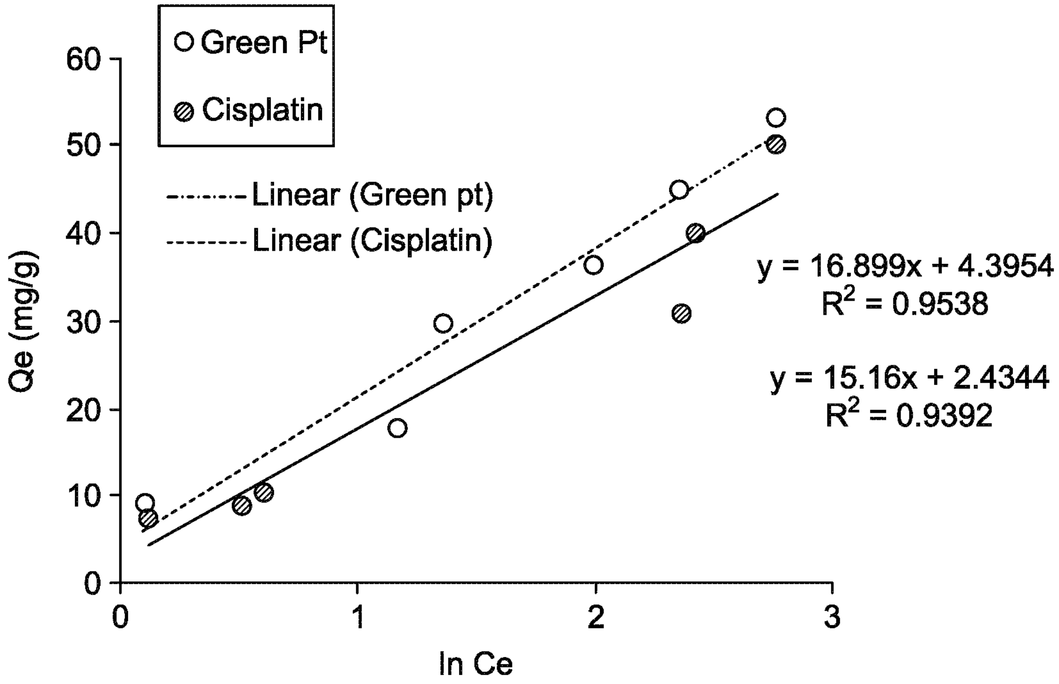
FIG. 7C depicts Temkin isotherm sorption of GPt and CPt by nanocarriers, according to certain embodiments.

The adsorption of cisplatin onto the nanocarrier was thus investigated with the help of a linearly established plot of the Temkin, Langmuir, and Freundlich isotherm simulations. The current study demonstrated the distribution method of the adsorbed molecules in the equilibrium state between both the solid and liquid phases, which is referred to as isothermal adsorption. Adsorption isotherms are helpful in studying the interactions in the adsorption process. FIGS. 7A-7C demonstrate the Langmuir, Freundlich, and Temkin isotherm models applied to determine the appropriate isotherm required for green Pt and cisplatin adsorption onto the nanocarrier samples.

Langmuir isotherm is used to describe adsorption process on a homogeneous surface, consisting of monolayer coverage, without any interactions among the adsorbate (ions). The equation below represents the linear form of the Langmuir isotherms. RL is the separation factor, and the RL value given in the equation reflects the favorability of the adsorption process, as follows:

$$R_L = 1/1 + C_0 K_L$$

The $R_L$ value ranges between 0 and 1, and depending on the value, the adsorption is considered as follows: $0<R_L<1$: favorable, $R_L=0$: irreversible, $R_L=1$: linear, $R_L>1$: unfavorable. FIG. 7A shows the linear Langmuir isotherm plots for green Pt and cisplatin onto nanocarrier samples. As shown in Table 3, the $R_L$ value was 0.356 for green Pt and 0.318 for cisplatin, indicating the favorability of the adsorption process. Moreover, $K_L$ (Langmuir adsorption constant) represents the affinity of the green Pt and cisplatin samples towards the cations. In the case of green Pt and cisplatin, the values are 0.090 and 0.106, respectively. The maximum adsorption capacity $q_0$ (mg/g) calculated by the Langmuir isotherm is 90.909 mg/g and 294.117 mg/g for GPt and cisplatin, respectively, onto the nanocarrier sample. The chemical composition with cisplatin obtained a higher cation exchange capacity than that with green Pt.

Freundlich isotherm equation proposes that as the concentration of the solution increases, the concentration of adsorbate on the surface increases. The assumption for this isotherm model is the heterogeneous adsorptive energies on the surface of the adsorbent. The linear form of the Freundlich isotherm is given in the following equation:

$$Q_e = K_F C_e^{1/n}$$

The adsorption parameters of the Freundlich isotherm for green Pt and cisplatin onto the nanocarrier are listed in Table 3. The values of the Freundlich constants were calculated by plotting the log $C_e$ against $q_e$, as shown in FIG. 7B. The $K_F$ value represents the adsorption ability (capacity), showing a significant difference between GPt and cisplatin onto the nanocarrier, with values of 2.265 mg/g and 0.081 mg/g for GPt and cisplatin, respectively. The nanocarrier sample had the highest adsorption capacity, due to its larger surface area, as well as its mesoporous nature. The other Freundlich constant n was in the limit between 1 and 10 and ranged from 0.964 to 2.871, indicating the favorability of adsorption of green Pt and cisplatin onto nanocarrier samples.

The Temkin isotherm model states that when the adsorbent coverage increases, the adsorption heat of all molecules in the layer decreases linearly. Temkin isotherm considers the indirect effect of adsorbate interactions on the adsorption process. The Temkin isotherm is applicable only at an intermediate range of ion concentrations. FIG. 7C shows the linear form of the Temkin isotherm. The linear form of the Temkin isotherm is given in the following equation:

$$q_e = (RT/b)\ln AC_e$$

Table 3 clearly states that the heat of adsorption (B) using the Temkin isotherm was higher for green Pt than cisplatin. The values using green Pt and cisplatin are 16.899, and 15.160 (J/mol) for the nanocarrier, respectively. GPt obtained the highest value of (B), since it positively contributes to the adsorption. The maximum binding energy (A) had the same sequence of selectivity as well. Investigating the previous adsorption isotherms, one can state that the correlation coefficients $R_2$ for Langmuir, Freundlich, and Temkin isotherm parameters for green Pt are 0.912, 0.985, and 0.953, respectively, whereas they are 0.867, 0.787, and 0.939 for cisplatin, respectively. The Freundlich adsorption isotherm has been used successfully to model the effects of balance experiments for green Pt, but cisplatin has successfully been modeled with the Temkin adsorption isotherm.

Both the Freundlich and Temkin models were still high and slightly near unity, so that still presents confidence and provides evidence that the assumptions of these models could occur simultaneously. Consequently, the Freundlich isotherm and Temkin isotherm fit with the experimental data, assuming a physisorption process on a heterogeneous surface; in addition, the uptake continued forming multilayers that covered the surface of the samples. From the results, it can be seen that the prepared nanocarrier in the present study displays a good performance for the removal of platinum ions, which is related to the superior combination advantages of GPt.

ZIF-8/silica/GPt, GPt, ZIF-8/silica/Cp/PEG, and ZIF-8/silica/GPt/PEG. The treatment concentrations of Cp and GPt leaf extract were adjusted to reflect actual concentrations in the nanocomposite. Thus, cell viability results of the different treatment conditions within the same dose such as, first, second, third, and fourth dose are comparable. According to the present disclosure, the nanocarrier ZIF-8/silica resulted in low cytotoxicity at the lower doses of about 0.025 mg/mL and 0.05 mg/mL, while it exhibited a cytotoxic effect with further increase in dose on both MCF-7 and HFF. The addition of the chemotherapeutic drug (Cp) and green Pt(GPt), forming treatment groups ZIF-8/silica/Cp and ZIF-8/silica/GPt, resulted in a significant cytotoxicity in MCF7 cells in a dose-dependent manner, while the same nano-formulations showed a lower toxic effect in HFF cells than that seen in MCF7.

The different effects on both cell lines were seen in the half-maximal effective concentration ($EC_{50}$) values, as tabulated in Table 5. $EC_{50}$ values for ZIF-8/silica/Cp and ZIF-8/silica/GPt in MCF7 were 39.72 μg/mL and 62.11 μg/mL, respectively. $EC_{50}$ values for the same nano-formulations on HFF were 94.01 μg/mL and 75.05 μg/mL, respectively. After pegylation, treatment with ZIF-8/silica/Cp/PEG and ZIF-8/silica/GPt/PEG resulted in a slightly lower toxic effect compared to treatment with nano-formulations without PEG. This is due to PEG covering the external surface of the nano-formulations, which prevents the direct interaction of

TABLE 3

Langmuir, Freundlich, Temkin models and parameters for sorption of GPt and cisplatin

| | Langmuir Model | | | | Freundlich Model | | | Temkin Model | | |
|---|---|---|---|---|---|---|---|---|---|---|
| | $q_0$ (mg/g) | $K_L$ (L/mg) | $R_L$ (L/mg) | $R_2$ | $K_f$ (mg/g) | n | $R^2$ | B (J/mol) | A (L/g) | $R^2$ |
| GreenPt | 90.909 | 0.09 | 0.356 | 0.912 | 2.265 | 0.964 | 0.985 | 16.899 | 1.296 | 0.953 |
| Cisplatin | 294.117 | 0.106 | 0.318 | 0.867 | 0.081 | 2.871 | 0.787 | 15.16 | 1.174 | 0.939 |

Figure 8:
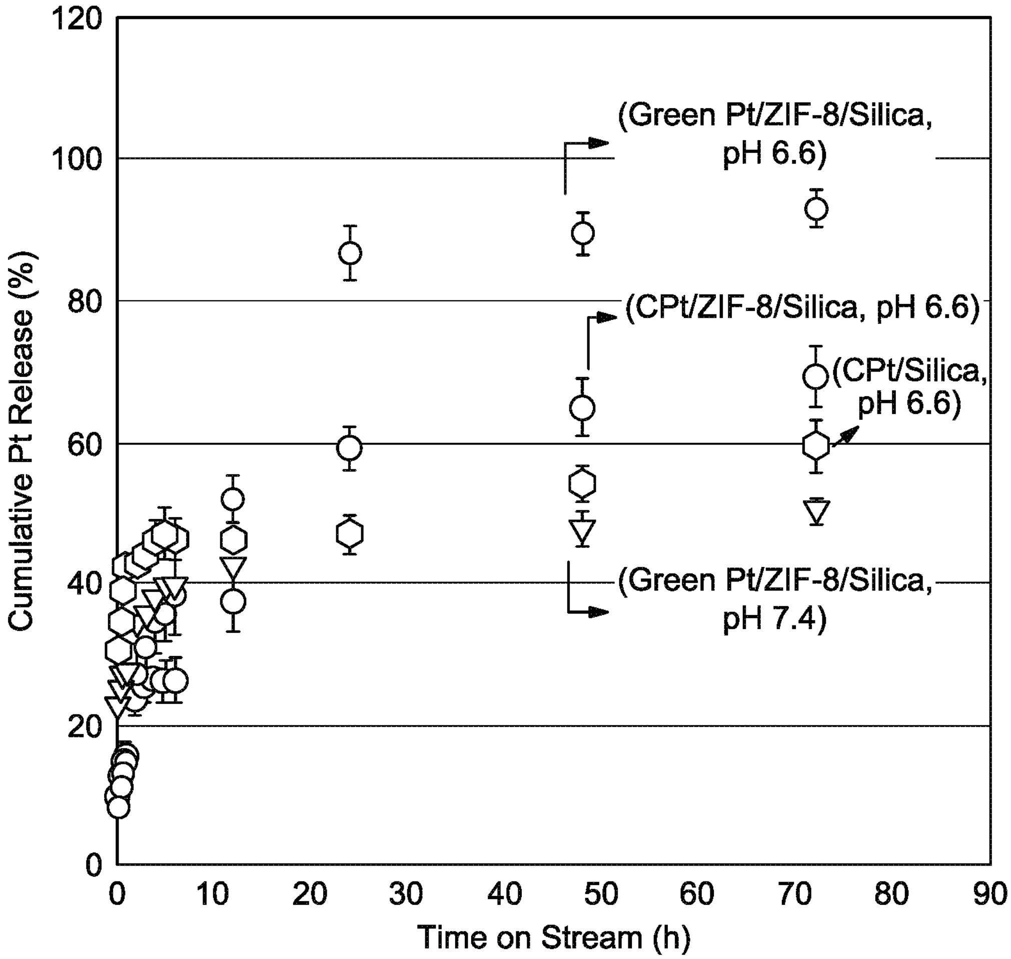
FIG. 8 depicts the drug release profile of Pt from CPt (ZIF-8/silica/CPt)-functionalized ZIF-8/silica nanocomposite, silica/CPt-functionalized ZIF-8/silica nanocomposite, and GPt (ZIF-8/Silica/GPt)-functionalized ZIF-8/silica nanocomposite, according to certain embodiments.

The pH stimulus-responsive nature of ZIF-8/Silica/GPt was studied in two pH conditions (pH 6.6 and 7.4) using phosphate-buffered solutions, as shown in FIG. 8. pH 6.6 mimics the pH of the tumor microenvironment, while pH 7.4 mimics the normal physiological condition. The release of Pt was analysed using calibrated curve for PtNPs. In general, the drug release profile shows an initial burst release due to loosely adsorbed drug molecules on the nanocarrier surface, followed by a sustained release. According to the present disclosure, under the tumor pH of 6.6, a high GPt release of about 93% was observed after 72 h. The release was observed to be higher than cisplatin-bound nano-formulation ZIF-8/silica/CPt and silica alone, which showed 70% and 60% CPt release after 72 h. In case of normal physiological pH of 7.4, a slower release of GPt was observed, with a percentage cumulative release of 50% after 72 h. The observed reduced GPt release at normal pH indicates the pH stimulus property of ZIF-8/silica nanocomposite and the structural stability of ZIF-8. In addition, the absence of burst release and the reduced GPt release at pH 7.4 minimize the toxic release of PtNPs that affect the healthy cells.

Figure 9A:
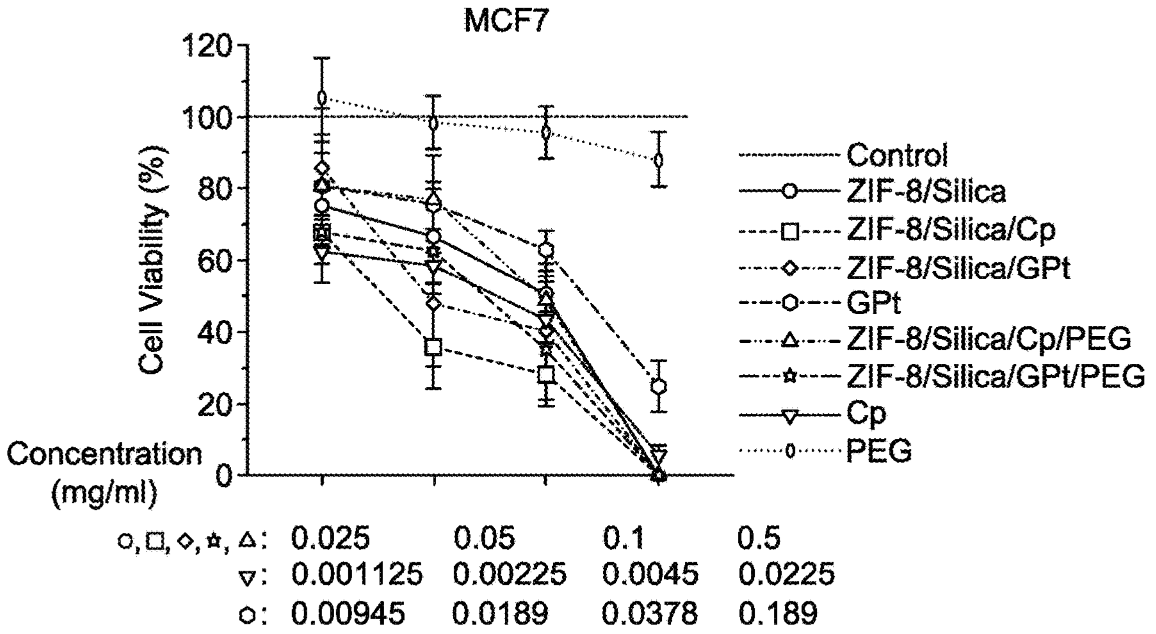
FIG. 9A depicts the percentage cell viability of a human mammary adenocarcinoma cell line (MCF-7) when treated with different nanocomposites, according to certain embodiments.
Figure 9B:
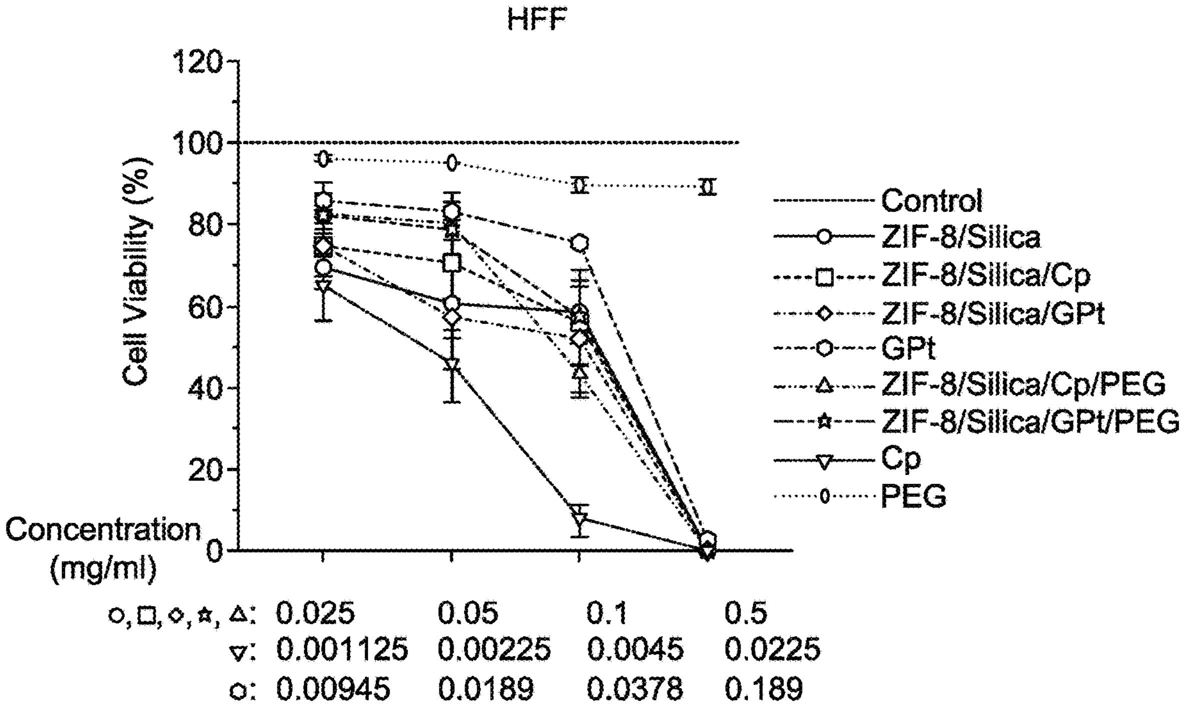
FIG. 9B depicts the percentage cell viability of human foreskin fibroblasts (HFFs) when treated with different nanocomposites, according to certain embodiments.
Figure 10A:
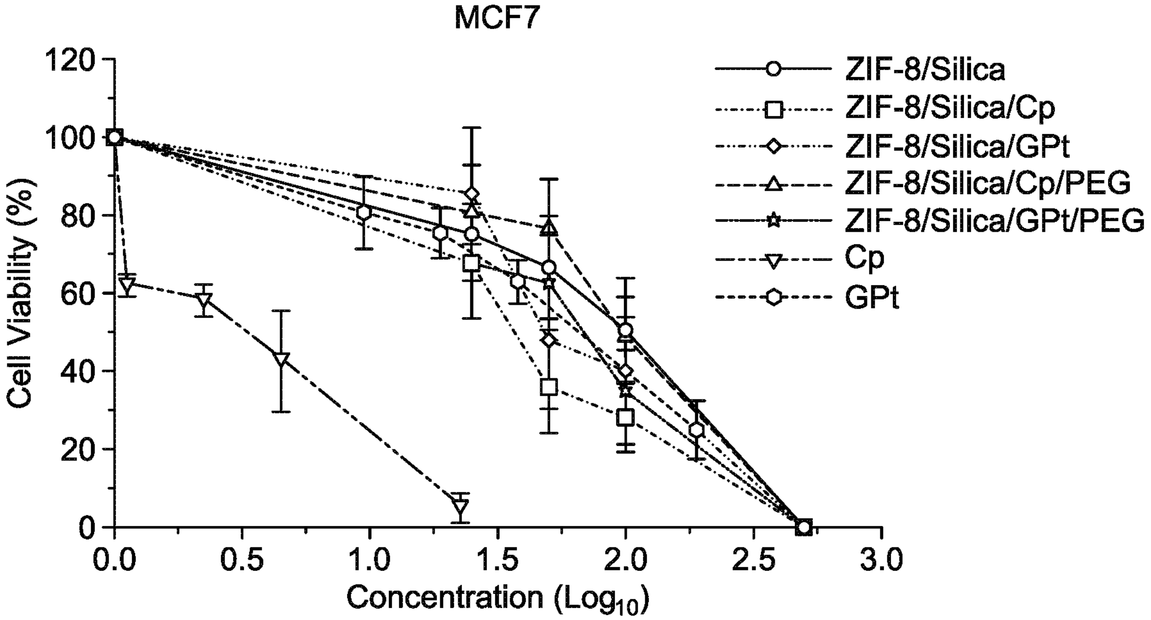
FIG. 10A depicts data from the cell viability assay presented in a log scale of MCF-7 when treated with ZIF-8/silica, ZIF-8/silica/Cp, ZIF-8/silica/GPt, ZIF-8/silica/Cp/PEG, ZIF-8/silica/GPt/PEG, Cp, and GPt for 48 h, according to certain embodiments.
Figure 10B:
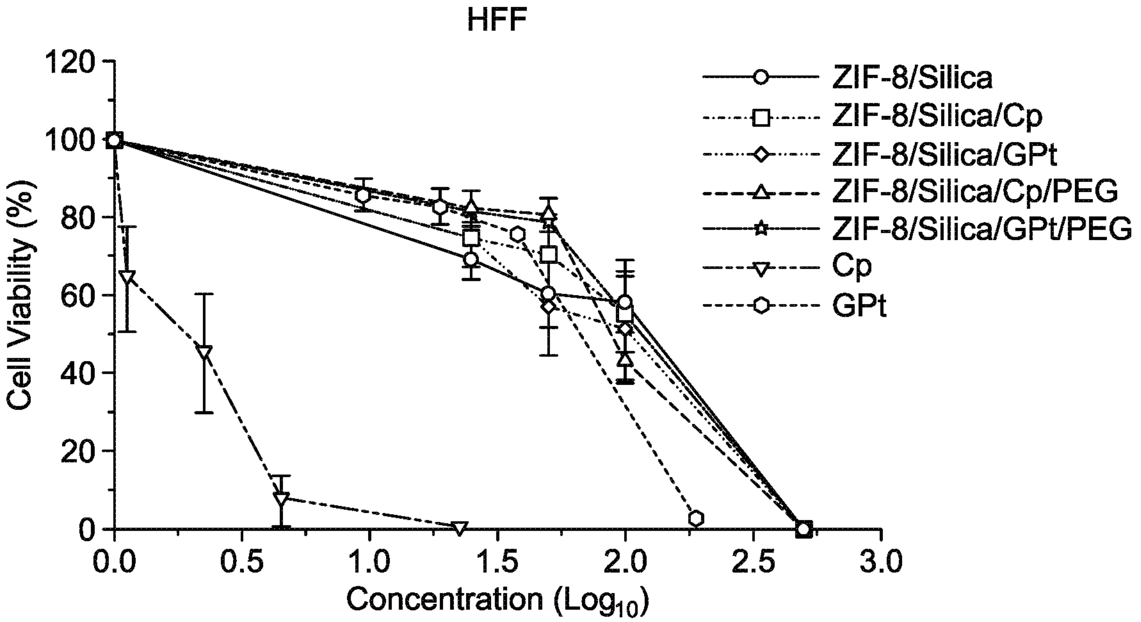
FIG. 10B depicts data from the cell viability assay presented in a log scale of HFF cells when treated with ZIF-8/silica, ZIF-8/silica/Cp, ZIF-8/silica/GPt, ZIF-8/silica/Cp/PEG, ZIF-8/silica/GPt/PEG, Cp, and GPt for 48 h, according to certain embodiments.

The cell viability assay (MTT) was performed on MCF7 and HFF cells to compare the cytotoxic efficacy of cisplatin versus the GPt loaded ZIF-8/silica nanocomposite, as shown in FIGS. 9A-9B and the statistical analysis in Tables 4A-4D (FIGS. 10A-10B). Cells were treated with the following nano-formulations: ZIF-8/silica (control), ZIF-8/silica/Cp, Pt with cells. However, increasing the dose to 0.1 and 0.5 mg/mL resulted in a significant reduction in cell viability. Although treatment with the pegylated Cp nano-formulation resulted in similar cell viability % in both cell lines, pegylated GPt nano-formulation resulted in better viability in HFF compared to that in MCF7. In MCF7 cells, ZIF-8/silica/GPt/PEG resulted in the following cell viability: 67.69%, 62.73%, and 34.92% for 0.025, 0.05, and 0.1 mg/mL, respectively. However, the same conditions in HFF resulted in the following viability: 81.86%, 78.64%, and 57.38% for 0.025, 0.05, and 0.1 mg/mL, respectively. The results showed that MCF7 cells treated with ZIF-8/silica/Cp/PEG and ZIF-8/silica/GPt/PEG had an $EC_{50}$ of 94.86 μg/mL and 60.19 μg/mL, respectively.

The statistical analysis on MCF7 (A, B) and HFF (C, D) was compared to the "no treatment control" (A, C) and cisplatin (B, D), in which the same corresponding concentrations were used, such as, the first dose of the nanocomposites was compared to the first dose of cisplatin and documented in Table 4A-4D. The green Pt compound activity was comparable to the chemotherapeutic drug cisplatin, thus providing a breakthrough in identifying a new Pt compound that is as active as cisplatin.

TABLE 4A

MCF7 Statistical Analysis compared to the "no treatment" control

| | Concentration | | | | | | | |
|---|---|---|---|---|---|---|---|---|
| | 0.025 mg/ml | | 0.05 mg/ml | | 0.1 mg/ml | | 0.5 mg/ml | |
| Treatment Group | Significant | P value | Significant | P value | Significant | P value | Significant | P value |
| ZIF-8/silica | No | 0.2338 | No | 0.3416 | No | 0.183 | Yes | 0.0001 |
| ZIF-8/silica/Cp | No | 0.0579 | No | 0.093 | Yes | 0.0427 | Yes | 0.0001 |
| ZIF-8/silica/GPt | No | 0.9076 | No | 0.273 | No | 0.2407 | Yes | 0.0001 |
| ZIF-8/silica/Cp/PEG | No | 0.6002 | No | 0.4905 | Yes | 0.0208 | Yes | 0.0001 |
| ZIF-8/silica/GPt/PEG | No | 0.3931 | No | 0.2588 | No | 0.1531 | Yes | 0.0001 |
| | | 0.001125 mg/ml | 0.00225 mg/ml | | 0.0045 mg/ml | | 0.0225 mg/ml | |
| Cp | Yes | 0.0147 | Yes | 0.0288 | No | 0.1347 | Yes | 0.0045 |
| | | 0.00945 mg/ml | 0.0189 mg/ml | | 0.0378 mg/ml | | 0.189 mg/ml | |
| GPt | No | 0.4415 | No | 0.1752 | No | 0.0638 | Yes | 0.0275 |

TABLE 4B

MCF7 Statistical Analysis compared to cisplatin

| | Concentration | | | | | | | |
|---|---|---|---|---|---|---|---|---|
| | 0.025 mg/ml | | 0.05 mg/ml | | 0.1 mg/ml | | 0.5 mg/ml | |
| Treatment Group | Significant | P value | Significant | P value | Significant | P value | Significant | P value |
| ZIF-8/silica | No | 0.5753 | No | 0.972 | No | 0.9975 | No | 0.7141 |
| ZIF-8/silica/Cp | No | 0.7941 | No | 0.5291 | No | 0.8909 | No | 0.7141 |
| ZIF-8/silica/GPt | No | 0.6795 | No | 0.9861 | No | >0.9999 | No | 0.7141 |
| ZIF-8/silica/Cp/PEG | No | 0.5764 | No | 0.594 | No | 0.9886 | No | 0.7141 |
| ZIF-8/silica/GPt/PEG | No | 0.9967 | No | 0.9983 | No | 0.9989 | No | 0.7141 |
| | | 0.001125 mg/ml | 0.00225 mg/ml | | 0.0045 mg/ml | | 0.0225 mg/ml | |
| Cp vs. control | Yes | 0.0147 | Yes | 0.0288 | No | 0.1346 | Yes | 0.0045 |
| | | 0.00945 mg/ml | 0.0189 mg/ml | | 0.0378 mg/ml | | 0.189 mg/ml | |
| GPt | No | 0.457 | No | 0.3218 | No | 0.6489 | No | 0.2982 |

TABLE 4C

HFF Statistical Analysis compared to the "no treatment" control

| | Concentration | | | | | | | |
|---|---|---|---|---|---|---|---|---|
| | 0.025 mg/ml | | 0.05 mg/ml | | 0.1 mg/ml | | 0.5 mg/ml | |
| Treatment Group | Significant | P value | Significant | P value | Significant | P value | Significant | P value |
| ZIF-8/silica | No | 0.2338 | No | 0.3416 | No | 0.183 | Yes | 0.0001 |
| ZIF-8/silica/Cp | No | 0.0579 | No | 0.093 | Yes | 0.0427 | Yes | 0.0001 |
| ZIF-8/silica/GPt | No | 0.9076 | No | 0.273 | No | 0.2407 | Yes | 0.0001 |
| ZIF-8/silica/Cp/PEG | No | 0.6002 | No | 0.4905 | Yes | 0.0208 | Yes | 0.0001 |

TABLE 4C-continued

| HFF Statistical Analysis compared to the "no treatment" control | | | | | | | | |
|---|---|---|---|---|---|---|---|---|
| | Concentration | | | | | | | |
| | 0.025 mg/ml | | 0.05 mg/ml | | 0.1 mg/ml | | 0.5 mg/ml | |
| Treatment Group | Significant | P value | Significant | P value | Significant | P value | Significant | P value |
| ZIF-8/silica/GPt/PEG | No | 0.3931 | No | 0.2588 | No | 0.1531 | Yes | 0.0001 |
| | | 0.001125 mg/ml | 0.00225 mg/ml | | 0.0045 mg/ml | | 0.0225 mg/ml | |
| Cp | Yes | 0.0147 | Yes | 0.0288 | No | 0.1347 | Yes | 0.0045 |
| | | 0.00945 mg/ml | 0.0189 mg/ml | | 0.0378 mg/ml | | 0.189 mg/ml | |
| GPt | No | 0.4415 | No | 0.1752 | No | 0.0638 | Yes | 0.0275 |

TABLE 4D

| HFF Statistical Analysis compared to the "no treatment" control | | | | | | | | |
|---|---|---|---|---|---|---|---|---|
| | Concentration | | | | | | | |
| | 0.025 mg/ml | | 0.05 mg/ml | | 0.1 mg/ml | | 0.5 mg/ml | |
| Treatment Group | Significant | P value | Significant | P value | Significant | P value | Significant | P value |
| ZIF-8/silica | No | 0.9896 | No | 0.733 | Yes | 0.0409 | Statistical analysis cannot be performed since the percentage cell viability for Cp at 0.0225 mg/ml is equal to zero. | |
| ZIF-8/silica/Cp | No | 0.8695 | No | 0.3707 | No | 0.1029 | | |
| ZIF-8/silica/GPt | No | 0.7163 | No | 0.9412 | No | 0.2063 | | |
| ZIF-8/silica/Cp/PEG | No | 0.387 | No | 0.1255 | No | 0.0514 | | |
| ZIF-8/silica/GPt/PEG | No | 0.4071 | No | 0.1623 | No | 0.124 | | |
| | | 0.001125 mg/ml | 0.00225 mg/ml | | 0.0045 mg/ml | | | |
| Cp vs. control | No | 0.1292 | No | 0.0712 | Yes | 0.0049 | | |
| | | 0.00945 mg/ml | 0.0189 mg/ml | | 0.0378 mg/ml | | | |
| GPt | No | 0.2957 | No | 0.1083 | Yes | 0.0019 | | |

TABLE 5

| $EC_{50}$ values (µg/mL) for MCF7 and HFF cell lines | | |
|---|---|---|
| Treatment Group | $EC_{50}$ µg/mL MCF7 | |
| ZIF-8/silica | 83.04 | 82.02 |
| ZIF-8/silica/Cp | 39.72 | 94.01 |
| ZIF-8/silica/GPt | 62.11 | 75.05 |
| ZIF-8/silica/Cp/PEG | 94.86 | 90.06 |
| ZIF-8/silica/GPt/PEG | 60.19 | 107.6 |
| Cp | 2.849 | 1.965 |
| GPt | 31.47 | 55.09 |

Numerous modifications and variations of the present disclosure are possible in light of the above teachings. It is therefore to be understood that within the scope of the appended claims, the invention may be practiced otherwise than as specifically described herein.

The invention claimed is:

1. A drug delivery system, comprising:
a zeolitic imidazolate framework-8 (ZIF-8);
silica;
platinum nanoparticles; and
polyethylene glycol,
wherein the silica penetrates pores of the ZIF-8 and at least partially envelopes the ZIF-8 to form a ZIF-8/silica composite,
wherein the platinum nanoparticles are present on a surface of the ZIF-8/silica composite, and
wherein the polyethylene glycol surrounds the platinum nanoparticles present on the surface of the ZIF-8/silica composite.

2. The drug delivery system of claim 1, wherein particles of the drug delivery system have an average size of 100-200 nm.

3. The drug delivery system of claim 1, wherein the platinum nanoparticles are spherical.

4. The drug delivery system of claim 1, wherein the platinum nanoparticles have an average size of 4-10 nm.

5. The drug delivery system of claim 1, wherein the platinum nanoparticles comprise $Pt^0$.

6. The drug delivery system of claim 1, wherein the platinum nanoparticles have a face-centered cubic crystal structure.

7. The drug delivery system of claim 1, wherein neem extract is bound to a portion of the platinum nanoparticles.

8. The drug delivery system of claim 1, wherein the platinum nanoparticles form aggregates, and wherein the aggregates have an average size of 50-100 nm.

9. The drug delivery system of claim 1, wherein the ZIF-8/silica composite has BET surface area of 50-100 $m^2/g$, and an average pore size of 20-25 nm.

10. The drug delivery system of claim 1, wherein the silica forms a shell around the ZIF-8 in the ZIF-8/silica composite.

11. The drug delivery system of claim 1, comprising C, Pt, Si, Zn, Cl, and O.

12. The drug delivery system of claim 1, having a zeta potential of −20 to −30 mV.

13. The drug delivery system of claim 1, wherein the ZIF-8/silica composite has a maximum adsorption capacity for the platinum nanoparticles of 80-100 mg per gram of the ZIF-8/silica composite.

14. The drug delivery system of claim 1, wherein 80-100% of the platinum nanoparticles are released from the drug delivery system in an environment having a pH of 6.6 after 72 hours.

15. The drug delivery system of claim 1, having an $EC_{50}$ for human breast cancer cells of 55-65 μg/mL.

16. The drug delivery system of claim 1, wherein the drug delivery system has an $EC_{50}$ that is lower than an $EC_{50}$ for a same drug delivery system but with cisplatin instead of platinum nanoparticles.

17. The drug delivery system of claim 1, wherein the platinum nanoparticles are made by a method comprising:

forming a powder of neem leaves;

mixing the powder of neem leaves in water, heating and filtering to form an extract;

mixing cisplatin in water to form a platinum solution;

mixing the platinum solution and the extract for 10-20 hours to form a reaction solution; and separating the platinum nanoparticles from the reaction solution, wherein a portion of the extract is bound to a surface of the platinum nanoparticles, and wherein the platinum nanoparticles are aggregated.

18. The drug delivery system of claim 17, wherein the platinum nanoparticles are spherical.

19. The drug delivery system of claim 18, wherein the platinum nanoparticles have an average size of 4-10 nm.

* * * * *